(12) United States Patent
Hulett et al.

(10) Patent No.: US 9,540,423 B2
(45) Date of Patent: Jan. 10, 2017

(54) PLANT DEFENSINS AND USE IN THE TREATMENT OF PROLIFERATIVE DISEASES

(71) Applicants: Balmoral Australia Pty Ltd, St Leonards, NSW (AU); Hexima Limited, Melbourne, VIC (AU)

(72) Inventors: Mark Darren Hulett, Eltham (AU); Fung Tso Lay, Reservoir (AU)

(73) Assignees: BALMORAL AUSTRALIA PTY LTD, St. Leonards (AU); HEXIMA LIMITED, Melbourne (AU)

( * ) Notice: Subject to any disclaimer, the term of this patent is extended or adjusted under 35 U.S.C. 154(b) by 0 days.

(21) Appl. No.: 14/352,360

(22) PCT Filed: Oct. 19, 2012

(86) PCT No.: PCT/AU2012/001267
§ 371 (c)(1),
(2) Date: Apr. 17, 2014

(87) PCT Pub. No.: WO2013/056309
PCT Pub. Date: Apr. 25, 2013

(65) Prior Publication Data
US 2015/0158918 A1   Jun. 11, 2015

Related U.S. Application Data

(60) Provisional application No. 61/548,825, filed on Oct. 19, 2011.

(51) Int. Cl.
*C07K 14/415* (2006.01)
*A61K 38/16* (2006.01)
*A61K 38/00* (2006.01)

(52) U.S. Cl.
CPC ............ *C07K 14/415* (2013.01); *A61K 38/00* (2013.01); *A61K 38/168* (2013.01); *C07K 2319/00* (2013.01)

(58) Field of Classification Search
None
See application file for complete search history.

(56) References Cited

U.S. PATENT DOCUMENTS

| | | | |
|---|---|---|---|
| 7,186,561 B2 | 3/2007 | da Costa e Silva et al. | |
| 7,572,436 B1 * | 8/2009 | Vernon ................ | A61K 38/168 424/278.1 |
| 2004/0250310 A1 | 12/2004 | Shukla et al. | |
| 2007/0207209 A1 | 9/2007 | Murphy et al. | |
| 2012/0172313 A1 | 7/2012 | Hulett et al. | |

FOREIGN PATENT DOCUMENTS

| | | |
|---|---|---|
| WO | 02063011 A1 | 8/2002 |
| WO | WO 0263011 A1 * | 8/2002 |
| WO | WO 02063011 A1 * | 8/2002 |
| WO | 2011160174 A1 | 12/2011 |

OTHER PUBLICATIONS

Guzmán-Rodríguez et al., "Plant Antimicrobial Peptides as Potential Anticancer Agents", BioMed Research Internationa, 2015, pp. 1-11.*
Stotz et al., Plant defensins: Defense, development and application:, Plant Signaling and Behavior, 2009, pp. 1010-1012.*
International Preliminary Report on Patentability dated Feb. 6, 2014 in connection with PCT/AU2012/001267.
Sagaram, Uma Shankar, et al. "Structure-activity determinants in antifungal plant defensins MsDef1 and MtDef4 with different modes of action against Fusarium graminearum." PLoS One 6.4 (2011): e18550.
Lin, Ku-Feng, et al. "Structure—based protein engineering for α—amylase inhibitory activity of plant defensin." Proteins: Structure, Function, and Bioinformatics 68.2 (2007): 530-540.
Anaya-Lopez, JoséL., et al. "Fungicidal and cytotoxic activity of a Capsicum chinense defensin expressed by endothelial cells." Biotechnology Letters 28.14 (2006): 1101-1108.
Van Der Weerden, Nicole L., and Marilyn A. Anderson. "Plant defensins: common fold, multiple functions." Fungal Biology Reviews 26.4 (2013): 121-131.
Loeza-Angeles, Heber, et al. "Thionin Thi2. 1 from Arabidopsis thaliana expressed in endothelial cells shows antibacterial, antifungal and cytotoxic activity." Biotechnology Letters 30.10 (2008): 1713-1719.
Lonez, Caroline, Michel Vandenbranden, and Jean-Marie Ruysschaert. "Cationic lipids activate intracellular signaling pathways." Advanced drug delivery reviews 64.15 (2012): 1749-1758.
Thomma, Bart P., Bruno P. Cammue, and Karin Thevissen. "Plant defensins." Planta 216.2 (2002): 193-202.
Lay, F. T., and M. A. Anderson. "Defensins-components of the innate immune system in plants." Current Protein and Peptide Science 6.1 (2005): 85-101.
Supplemental European Search Report for European Patent Application No. 11797388.3 dated Oct. 11, 2013.
International Search Report for International Application No. PCT-AU2011/000760 dated Aug. 2, 2011.
Written Opinion of the International Searching Authority for International Application No. PCT/AU2011/000760 dated Aug. 2, 2011.
Sporn, Michael B. "Dichotomies in cancer research: some suggestions for a new synthesis." Nature Clinical Practice Oncology 3.7 (2006): 364-373.

(Continued)

*Primary Examiner* — Lianko Garyu
(74) *Attorney, Agent, or Firm* — Quarles & Brady LLP

(57) ABSTRACT

The present invention relates to compositions and methods for preventing or treating proliferative diseases. In particular, the present invention relates to the use of compositions derived or derivable from plants, such as plant defensins, particularly in methods for the prevention or treatment of proliferative diseases such as cancer. The present invention also relates to associated uses, systems and kits.

2 Claims, 8 Drawing Sheets

(56) References Cited

OTHER PUBLICATIONS

Detailed Guide: Melanoma Skin Cancer, American Cancer Society, Cancer.Org, Last revised Sep. 20, 2012, attached as pdf, also available at http://www.cancer.org/cancer/skincancer-melanoma/detailedguide/melanoma-skin-cancer-prevention, last visited Nov. 5, 2012.

Lay, Fung T., et al. "The three-dimensional solution structure of NaD1, a new floral defensin from Nicotiana alata and its application to a homology model of the crop defense protein alfAFP." Journal of molecular biology 325.1 (2003): 175-188.

Pshenichnov, E. A., et al. "Bioactive protein components from Hibiscus esculentus seeds." Chemistry of natural compounds 41.1 (2005): 82-84.

Charlton, Anne. "Medicinal uses of tobacco in history." Journal of the Royal Society of Medicine 97.6 (2004): 292-296.

Meyers, Christina A. "How chemotherapy damages the central nervous system Christina A Meyers." Journal of biology 7 (2008): 11.

Lens, Marko B., and Tim G. Eisen. "Systemic chemotherapy in the treatment of malignant melanoma." Expert opinion on pharmacotherapy 4.12 (2003): 2205-2211.

Thomma, Bart PHJ, Bruno PA Cammue, and Karin Thevissen. "Mode of action of plant defensins suggests therapeutic potential." Current Drug Targets-Infectious Disorders 3.1 (2003): 1-8.

Van Der Weerden, Nicole L., Fung T. Lay, and Marilyn A. Anderson. "The plant defensin, NaD1, enters the cytoplasm of Fusarium oxysporum hyphae." Journal of Biological Chemistry 283.21 (2008): 14445-14452.

Crawford, Jeffrey, David C. Dale, and Gary H. Lyman. "Chemotherapy—induced neutropenia." Cancer 100.2 (2004): 228-237.

Ajesh, K., and K. Sreejith. "Peptide antibiotics: an alternative and effective antimicrobial strategy to circumvent fungal infections." Peptides 30.5 (2009): 999-1006.

Matejuk, A., et al. "Peptide-based antifungal therapies against emerging infections." Drugs of the Future 35.3 (2010): 197.

* cited by examiner

FIGURE 2B

```
                                          10        20        30        40        50
                                     ....|....|....|....|....|....|....|....|....|....|
         NoD173   (N. occidentalis)  ---RQCKAESNTFTGICIAKPPCRQACIR--EK---FTDGHCSKV---LPRCLCTKPC      SEQ ID NO:3
         NaD1     (N. alata)         ---RECKTESNTFPGICITKPPCRKACIS--EK---FTDGHCSKI---LPRCLCTKPC      SEQ ID NO:11
         NsD1     (N. suaveolens)    ---KDCKRESNTFPGICITKPPCRKACIR--EK---FTDGHCSKI---LPRCLCTKPC      SEQ ID NO:12
         NsD2     (N. suaveolens)    ---KDCKRESNTFPGICITKLPCRKACIS--EK---FADGHCSKI---LPRCLCTKPC      SEQ ID NO:13
         FST      (N. tabacum)       ---RECKTESNTFPGICITKPPCRKACIS--EK---FTDGHCSKL--LPRCLCTKPC       SEQ ID NO:14
         NeThio1  (N. excelsior)     ---RECARE--ISTGLCITNPQCRKACIK--EK---FTDGHCSKI---LPRCLCTKPC      SEQ ID NO:15
         NeThio2  (N. excelsior)     ---KDCKTESNTFPGICITKPPCRKACIR--EK---FTDGHCSKI---LPRCLCTKPC      SEQ ID NO:16
Class II Na-gth   (N. attenuata)     -KSTCKAESNTFEGFCVTKPPCRRACLK--EK---FTDGKCSKI---LRRCICYKPC      SEQ ID NO:17
         NpThio1  (N. paniculata)    -KSTCKAESNTFPGLCITKPPCRKACLS--EK---FTDGKCSKI---LRPCICYKPC      SEQ ID NO:18
         NgD137   (N. goodspeedii)   --RDCKTESNTFPGICITKPPCRKACIR--EK---FTDGHCSKI---LRKCLCTKPC      SEQ ID NO:19
         NmD12    (N. megalosiphon)  --RQCKAESNTFTGICIAKPPCRKACIR--EK---FTDGHCSKV---LRRCLCTKKC      SEQ ID NO:20
         NmD16    (N. megalosiphon)  --RQCKAESNTFTGICIAKPPCRKACIR--EK---FTDGHCSKV---LRKCLCTKPC      SEQ ID NO:21
         TPP3     (S. lycopersicum)  -QQICKAPSQTFPGLCFMDSSCRKYCIK--EK---FTGGHCSKL--QRKCLCTKPC       SEQ ID NO:22
         PhD1     (P. hybrida)       --ATCKAECPFTWDSVCINKKPCVACCKK---AK--FSDGHCSKI---LRRCLCTKEC     SEQ ID NO:23
         PhD2     (P. hybrida)       --GTCKAECPTWEGICINKAPCVKCCKAQPEK--FTDGHCSKI---LRRCLCTKPC       SEQ ID NO:24
         Cc-gth   (C. chinense)      QNNICKTFSKHFKGLCFADSKCRKVCIQ-EDK---FEDGHCSKL--QRKCLCTKNC       SEQ ID NO:25
         CaD3301  (C. annuum)        --NICKTKSKYFEGLCWVDSSCRKVCIE-KDK---FEDGHCSKL---LRNCLCTKIC      SEQ ID NO:26
         CcD4509  (C. chinense)      -QNICKTPFSKYFKGLCITDSSCRKVCIE-KDK---FEDGHCSKI---LRKCLCTKIC     SEQ ID NO:27
         CfD5321  (C. frutescens)    -QNICKTKSKYFTGLCWTDSSCRKVCIE-KDK---FQDGHCSKI---QRNCLCTKIC      SEQ ID NO:28
         CbD1260  (C. baccatum)      -QNICKTPFSKYFKGLCITDSSCRKVCIE-KDK---FEDGHCSKL--QRKCLCTKIC      SEQ ID NO:29
         CcD1338  (C. chinense)      -KNICKTISKYYKGLCITDSSCRKVCIE-KDK---FQDGHCRKL--QRKCLCTKIC       SEQ ID NO:30

NaD2     (N. alata)         --RTCESQSHRFKGPCARDSNCATVCLT---E--GPSGGDCRG-F-RRRCFCTRPC       SEQ ID NO:31
         NsD3     (N. suaveolens)    --RTCESQSHRFKGPCSRDSNCATVCLT--E--GPSGGDCRG-F-RRRCFCTRPC        SEQ ID NO:32
         PPT      (P. inflata)       --RTCESQSHRFHGTCVRESNCASVCQT--E--GPIGGNCRA-F-RRRCFCTRNC        SEQ ID NO:33
         TGAS118  (S. lycopersicum)  --RTCESQSHRFKGPCVSEKNCASVCET---E--GPSGGDCRGFFFS--CFCTRPC       SEQ ID NO:34
         P322     (S. tuberosum)     --RHCESLSHRFKGPCTRDSNCASVCET--ER--FSGGNCRG-F-RRRCFCTKPC        SEQ ID NO:35
         SE60     (G. max)           --RVCESQSHGFHGLCNRDHNCALVCRN--E--GPSGGNCHG-F-RRRCFCTRIC        SEQ ID NO:36
Class I  SIα1     (S. bicolor)       ---RVCMKGSQHHSFPCISDRLCSNECVK--EE-GGWTAGYCH----LPYCRCQKAC     SEQ ID NO:37
         γ1-H     (H. vulgare)       --RICRRRSAGFKGPCVSNKNCAQVCMQ--E--GWGGGNCDGP--LRRCKCMRRC        SEQ ID NO:38
         γ1-P     (T. turgidium)     --KICRRRSAGFKGPCMSNKNCAQVCQQ--E--GWGGGNCDGPF--RRCKCIRQC        SEQ ID NO:39
         MsDef1   (M. sativus)       --RTCENLADKYRGPCFS-G--CDTHCTT-KE--NAVSGRCRDDF---RCWCTKRC       SEQ ID NO:40
         SD2      (H. annuus)        --RTCESQSHKFKGTCLSDTNCANVCHS--ER--FSGGKCRG-F-RRRCFCTTHC        SEQ ID NO:41
         Psd1     (P. sativum)       --KTCEHLADTYRGVCFTNASCDDHCKN--KAH--LISGTCHN-W---KCFCTQNC       SEQ ID NO:42
         γ2-Z     (Z. mays)          ---RVCMGKSQHHSFPCISDRLCSNECVK--EDGGWTAGYCH----LRYCRCQKAC      SEQ ID NO:43
         Rs-AFP2  (R. sativus)       -ZKLCQRPSGTWSGVCGNNNACKNQCIRL-EK---ASHGSCNYVFPAHKCICYFPC       SEQ ID NO:44
         Hs-AFP1  (H. sanguinea)     ---KLCDVPSGTWSGHCGSSSKCSQQCKDR-EH--FAYGGACHYQFPSVFCFCKRQC     SEQ ID NO:45
         Dm-AMP1  (D. merckii)       ---ELCEKASKTWSGNCGNTGHCDNQCKSW-E---GAAHGACHVRNGKHMCFCYFKC     SEQ ID NO:46
```

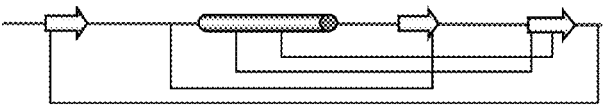

PLANT DEFENSINS AND USE IN THE TREATMENT OF PROLIFERATIVE DISEASES

CROSS-REFERENCE TO RELATED APPLICATIONS

This application claims priority to U.S. Provisional Patent Application No. 61/548,825 filed on 19 Oct. 2011, which is hereby incorporated by reference in its entirety

FIELD OF THE INVENTION

The present invention relates to compositions and methods for preventing or treating proliferative diseases. In particular, the present invention relates to the use of compositions derived or derivable from plants, such as plant defensins, particularly in methods for the prevention or treatment of proliferative diseases such as cancer. The present invention also relates to associated uses, systems and kits.

STATEMENT REGARDING FEDERALLY FUNDED RESEARCH

Not applicable.

BACKGROUND TO THE INVENTION

Plants are known to produce a variety of chemical compounds, either constitutively or inducibly, to protect themselves against environmental stresses, wounding, or microbial invasion.

Of the plant antimicrobial proteins that have been characterized to date, a large proportion share common characteristics. They are generally small (<10 kDa), highly basic proteins and often contain an even number of cysteine residues (typically 4, 6 or 8). These cysteines all participate in intramolecular disulfide bonds and provide the protein with structural and thermodynamic stability (Broekaert et al. (1997)). Based on amino acid sequence identities, primarily with reference to the number and spacing of the cysteine residues, a number of distinct families have been defined. They include the plant defensins (Broekaert et al., 1995, 1997; Lay et al., 2003a), thionins (Bohlmann, 1994), lipid transfer proteins (Kader, 1996, 1997), hevein (Broekaert et al., 1992) and knottin-type proteins (Cammue et al., 1992), as well as antimicrobial proteins from *Macadamia integrifolia* (Marcus et al., 1997; McManus et al., 1999) and *Impatiens balsamina* (Tailor et al., 1997; Patel et al., 1998) (Table 1). All these antimicrobial proteins appear to exert their activities at the level of the plasma membrane of the target microorganisms, although it is likely that the different protein families act via different mechanisms (Broekaert et al., 1997). The cyclotides are a new family of small, cysteine-rich plant peptides that are common in members of the Rubiaceae and Violaceae families (reviewed in Craik et al., 1999, 2004; Craik, 2001). These unusual cyclic peptides (Table 1) have been ascribed various biological activities including antibacterial (Tam, et al., 1999), anti-HIV (Gustafson et al., 1994) and insecticidal (Jennings et al., 2001) properties.

TABLE 1

Small, cysteine-rich antimicrobial proteins in plants.

| Peptide family | Representative member | No. of amino acids | Consensus sequence |
|---|---|---|---|
| Plant defensins | Rs-AFP2 | 51 | 3-C-10-C-5-C-3-C-9-C-8-C-1-C-3-C |
| α/β-Thionin (8-Cys type) | α-Purothionin | 45 | 2-CC-7-C-3-C-8-C-3-C-1-C-8-C-6 |
| Lipid transfer protein | Ace-AMP1 | 93 | 3-C-9-C-12-CC-18-C-1-C-23-C-15-C-4 |
| Hevein-type | Ac-AMP2 | 30 | 3-C-4-C-4-CC-5-C-6-C-2 |
| Knottin-type | Mj-AMP1 | 36 | 1-C-6-C-8-CC-3-C-10-C-3 |
| Macadamia | MiAMP1 | 76 | 10-C-9-C-1-C-25-C-14-C-11-C |
| Impatients | Ib-AMP1 | 20 | 5-CC-8-C-3-C |
| Cyclotide | Kalata B1 | 29 | 1-C-3-C-4-C-4-C-1-C-4-C-6 |

The size of the mature protein and spacing of cysteine residues for representative members of plant antimicrobial proteins is shown in Table 1. The numbers in the consensus sequence represent the number of amino acids between the highly conserved cysteine residues in the representative member but other members of the family may vary slightly in the inter-cysteine lengths. The disulfide connectivities are given by connecting lines. The cyclic backbone of the cyclotides is depicted by the broken line (from Lay and Anderson, 2005).

Defensins

The term "defensin" has previously been used in the art to describe a diverse family of molecules that are produced by many different species and which function in innate defense against pathogens including bacteria, fungi, yeast and viruses.

Plant Defensins

Plant defensins (also termed γ-thionins) are small (~5 kDa, 45 to 54 amino acids), basic proteins with eight cysteine residues that form four strictly conserved disulfide bonds with a $Cys_I$-$Cys_{VIII}$, $Cys_{II}$-$Cys_{IV}$, $Cys_{III}$-$Cys_{VI}$ and $Cys_V$-$Cys_{VII}$ configuration. As well as these four strictly conserved disulfide bonds, some plant defensins have an additional disulfide bond (Lay et al., 2003a, 2003b; Janssen et al., 2003).

The name "plant defensin" was coined in 1995 by Terras and colleagues who isolated two antifungal proteins from radish seeds (Rs-AFP1 and Rs-AFP2) and noted that at a primary and three-dimensional structural level these proteins were distinct from the plant α-/β-thionins but shared some structural similarities to insect and mammalian defensins (Terras et al., 1995; Broekaert et al., 1995).

Plant defensins exhibit clear, although relatively limited, sequence conservation. Strictly conserved are the eight cysteine residues and a glycine at position 34 (numbering relative to Rs-AFP2). In most of the sequences, a serine at position 8, an aromatic residue at position 11, a glycine at position 13 and a glutamic acid at position 29 are also conserved (Lay et al., 2003a; Lay and Anderson, 2005).

The three-dimensional solution structures of the first plant defensins were elucidated in 1993 by Bruix and colleagues for γ1-P and γ1-H. Since that time, the structures of other seed-derived and two flower-derived (NaD1 and PhD1) defensins have been determined (Lay et al., 2003b; Janssen et al., 2003). All these defensins elaborate a motif known as the cysteine-stabilized αβ (CSαβ) fold and share highly superimposable three-dimensional structures that comprise a well-defined α-helix and a triple-stranded antiparallel β-sheet. These elements are organized in a βαββ arrangement and are reinforced by four disulfide bridges.

The CSαβ motif is also displayed by insect defensins and scorpion toxins. In comparing the amino acid sequences of the structurally characterized plant defensins, insect defensins and scorpion toxins, it is apparent that the CSαβ scaffold is highly permissive to size and compositional differences.

The plant defensin/γ-thionin structure contrasts to that which is adopted by the α-and β-thionins. The α-and β-thionins form compact, amphipathic, L-shaped molecules where the long vertical arm of the L is composed of two α-helices, and the short arm is formed by two antiparallel β-strands and the last (~10) C-terminal residues. These proteins are also stabilized by three or four disulfide bonds (Bohlmann and Apel, 1991).

Plant defensins have a widespread distribution throughout the plant kingdom and are likely to be present in most, if not all, plants. Most plant defensins have been isolated from seeds where they are abundant and have been characterized at the molecular, biochemical and structural levels (Broekaert et al., 1995; Thomma et al., 2003; Lay and Anderson, 2005). Defensins have also been identified in other tissues including leaves, pods, tubers, fruit, roots, bark and floral tissues (Lay and Anderson, 2005).

An amino acid sequence alignment of several defensins that have been identified, either as purified protein or deduced from cDNAs, has been published by Lay and Anderson (2005). Other plant defensins have been disclosed in U.S. Pat. No. 6,911,577, International Patent Publication No. WO 00/11196 and International Patent Publication No. WO 00/68405, the entire contents of which are incorporated herein by reference.

Mammalian Defensins

The mammalian defensins form three distinct structural subfamilies known as the α-, β-and θ-defensins. In contrast to the plant defensins, all three subfamilies contain only six cysteine residues which differ with respect to their size, the placement and connectivity of their cysteines, the nature of their precursors and their sites of expression (Selsted et al., 1993; Hancock and Lehrer, 1998; Tang et al., 1999a, b; Lehrer and Ganz, 2002). All subfamilies have an implicated role in innate host immunity and more recently, have been linked with adaptive immunity as immunostimulating agents (Tang et al., 1999b; Lehrer and Ganz, 2002). It was in the context of their defense role that the name "defensin" was originally coined (Ganz et al., 1985; Selsted et al., 1985).

The α-defensins (also known as classical defensins) are 29-35 amino acids in length and their six cysteine residues form three disulfide bonds with a $Cys_I$-$Cys_{VI}$, $Cys_{II}$-$Cys_{IV}$ and $Cys_{III}$-$Cys_V$ configuration (Table 2).

In contrast to the α-defensins, the β-defensins are larger (36-42 amino acids in size) and have a different cysteine pairing ($Cys_I$-$Cys_V$, $Cys_{II}$-$Cys_{IV}$ and $Cys_{III}$-$Cys_{VI}$) and spacing (Tang and Selsted, 1993). They are also produced as preprodefensins. However, their prodomains are much shorter. Analogous to the α-defensins, the synthesis of β-defensins can be constitutive or can be induced following injury or exposure to bacteria, parasitic protozoa, bacterial lipopolysaccharides, and also in response to humoral mediators (i.e. cytokines) (Diamond et al., 1996; Russell et al., 1996; Tarver et al., 1998).

The size of the mature protein and spacing of cysteine residues for representative members of defensin and defensin-like proteins from insects and mammals is shown in Table 2. The numbers in the consensus sequence represent the number of amino acids between the highly conserved cysteine residues in the representative member, but other members of the family may vary slightly in the inter-cysteine lengths. The disulfide connectivities are given by connecting lines. The cyclic backbone of the mammalian theta-defensins is depicted by the broken line.

TABLE 2

Representative members of defensin and defensin-like proteins from insects and mammals

| Peptide family | Representative member | No. of amino acids | Consensus sequence | Reference |
|---|---|---|---|---|
| Insect defensin-like | Drosomycin | 44 | 1-C-8-C-7-C-3-C-9-C-5-C-1-C-2-C | Lamberty et al., 2001 |
| Insect defensin | Insect defensin A | 40 | 2-C-12-C-3-C-9-C-5-C-1-C-2 | Cornet et al., 1995 |
| Mammalian α-defensin | HNP-4 | 34 | 1-C-1-C-4-C-9-C-9-CC-4 | Harwig et al., 1992 |
| Mammalian β-defensin | HBD-1 | 36 | 4-C-6-C-4-C-9-C-6-CC-1 | Bensch et al., 1995 |

TABLE 2-continued

Representative members of defensin and defensin-like proteins from insects and mammals

| Peptide family | Representative member | No. of amino acids | Consensus sequence | Reference |
| --- | --- | --- | --- | --- |
| Mammalian θ-defensin | RTD-1 | 18 | 2-C-1-C-1-C-4-C-1-C-1-C-2 | Tang et al., 199a, b Trabi et al., 2001 |

Insect Defensins

A large number of defensin and defensin-like proteins have been identified in insects. These proteins are produced in the fat body (equivalent of the mammalian liver) from which they are subsequently released into the hemolymph (Lamberty et al., 1999). Most insect defensins have three disulfide bonds. However, a number of related proteins, namely drosomycin from *Drosophila melanogaster*, have four disulfides (Fehlbaum et al., 1994; Landon et al., 1997) (Table 2).

The three-dimensional structures of several insect defensins have been solved (e.g. Hanzawa et al., 1990; Bonmatin et al., 1992; Cornet et al., 1995; Lamberty et al., 2001; Da Silva et al., 2003). Their global fold, as typified by insect defensin A, features an α-helix, a double-stranded antiparallel β-sheet and a long N-terminal loop. These elements of secondary structure are stabilized by three disulfide bonds that are arranged in a $Cy_{sI}$-$Cy_{sIV}$, $Cy_{sII}$-$Cy_{sV}$ and $Cy_{sIII}$-$Cy_{sVI}$ configuration (Bonmatin et al., 1992; Cornet et al., 1995).

Two Classes of Plant Defensins

Plant defensins can be divided into two major classes according to the structure of the precursor proteins predicted from cDNA clones (Lay et al., 2003a) (FIG. 1). In the first and largest class, the precursor protein is composed of an endoplasmic reticulum (ER) signal sequence and a mature defensin domain. These proteins enter the secretory pathway and have no obvious signals for post-translational modification or subcellular targeting (FIG. 1A).

The second class of defensins are produced as larger precursors with C-terminal prodomains or propeptides (CT-PPs) of about 33 amino acids (FIG. 1B). Class II defensins have been identified in solanaceous species where they are expressed constitutively in floral tissues (Lay et al., 2003a; Gu et al., 1992; Milligan et al., 1995; Brandstadter et al., 1996) and fruit (Aluru et al., 1999) and in salt stressed leaves (Komori et al., 1997; Yamada et al., 1997). The CTPP of the solanaceous defensins from *Nicotiana alata* (NaD1) and *Petunia hybrida* (PhD1 and PhD2) is removed proteolytically during maturation (Lay et al., 2003a).

The CTPPs on the solanaceous defensins have an unusually high content of acidic and hydrophobic amino acids. Interestingly, at neutral pH, the negative charge of the CTPP counter-balances the positive charge of the defensin domain (Lay and Anderson, 2005).

Biological Activity of Plant Defensins

Some biological activities have been attributed to plant defensins including growth inhibitory effects on fungi (Broekaert et al., 1997; Lay et al., 2003a; Osborn et al., 1995; Terras et al., 1993), and Gram-positive and Gram-negative bacteria (Segura et al., 1998; Moreno et al., 1994; Zhang and Lewis, 1997). Some defensins are also effective inhibitors of digestive enzymes such as α-amylases (Zhang et al., 1997; Bloch et al., 1991) and serine proteinases (Wijaya et al., 2000; Melo et al., 2002), two functions consistent with a role in protection against insect herbivory. This is supported by the observation that bacterially expressed mung bean defensin, VrCRP, is lethal to the bruchid *Callosobruchus chinensis* when incorporated into an artificial diet at 0.2% (w/w) (Chen et al., 2002). Some defensins also inhibit protein translation (Mendez et al., 1990; Colilla et al., 1990; Mendez et al., 1996) or bind to ion channels (Kushmerick et al., 1998). A defensin from *Arabidopsis halleri* also confers zinc tolerance, suggesting a role in stress adaptation (Mirouze et al., 2006). More recently, a sunflower defensin was shown to induce cell death in Orobanche parasite plants (de Zélicourt et al., 2007).

Antifungal Activity

The best characterized activity of some but not all plant defensins is their ability to inhibit, with varying potencies, a large number of fungal species (for examples, see Broekaert et al., 1997; Lay et al., 2003a; Osborn et al., 1995). Rs-AFP2, for example, inhibits the growth of *Phoma betae* at 1 µg/mL, but is ineffective against *Sclerotinia sclerotiorum* at 100 µg/mL (Terras et al., 1992). Based on their effects on the growth and morphology of the fungus, *Fusarium culmorum*, two groups of defensins can be distinguished. The "morphogenic" plant defensins cause reduced hyphal elongation with a concomitant increase in hyphal branching, whereas the "non-morphogenic" plant defensins reduce the rate of hyphal elongation, but do not induce marked morphological distortions (Osborn et al., 1995).

More recently, the pea defensin Psd1 has been shown to be taken up intracellularly and enter the nuclei of *Neurospora crassa* where it interacts with a nuclear cyclin-like protein involved in cell cycle control (Lobo et al., 2007). For MsDef1, a defensin from alfalfa, two mitogen-activated protein (MAP) kinase signaling cascades have a major role in regulating MsDef1 activity on *Fusarium graminearum* (Ramamoorthy et al., 2007).

Permeabilization of fungal membranes has also been reported for some plant defensins (Lay and Anderson, 2005). For example, NaD1 is a plant defensin isolated from floral tissue of *Nicotiana alata*. The amino acid and coding sequences of NaD1 are disclosed in International Patent Publication No. WO 02/063011, the entire contents of which are incorporated by reference herein. NaD1 was tested in vitro for antifungal activity against the filamentous fungi *Fusarium oxysporum* f. sp. *vasinfectum* (Fov), *Verticillium dahliae, Thielaviopsis basicola, Aspergillus nidulans* and *Leptosphaeria maculans*. At 1 µM, NaD1 retarded the growth of Fov and *L. maculans* by 50% while *V. dahliae, T. basicola*, and *A. nidulans* were all inhibited by approximately 65%. At 5 µM NaD1, the growth of all five species was inhibited by more than 80%. These five fungal species are all members of the ascomycete phylum and are distributed among three classes in the subphylum pezizomycotiria.

These fungi are agronomically important fungal pathogens. All filamentous fungi tested thus far are sensitive to inhibition by NaD1 (van der Weerden et al., 2008).

The importance of the four disulfide bonds in NaD1 was investigated by reducing and alkylating the cysteine residues. Reduced and alkylated NaD1 (NaD1$_{R\&A}$) was completely inactive in the growth inhibitory assays with Fov, even at a concentration ten-fold higher than the IC$_{50}$ for NaD1 (van der Weerden et al., 2008).

Prior Work with Antimicrobial Peptides and Tumour Cells
Use of Small Cysteine-Rich/Cationic Antimicrobial Peptides in the Treatment of Human Disease There is an increasing body of literature implicating human α-and β-defensins in various aspects of cancer, tumourigenesis, angiogenesis and invasion. The use of mammalian defensins has also been proposed for the treatment of viral and fungal infections and as an alternative or adjunct to antibiotic treatment of bacterial infections. However, their cytotoxicity towards mammalian cells remains a significant barrier. Moss et al (U.S. Pat. No. 7,511,015) have shown that modification of the defensin peptide through ribosylation or ADP-ribosylation of arginine residues modifies the toxicity of the peptide and enhances its antimicrobial properties.

The review by Mader and Hoskin (2006) describes the use of cationic antimicrobial peptides as novel cytotoxic agents for cancer treatment. It should be noted however that a review by Pelegrini and Franco (2005) incorrectly describes α-/β-thionins from mistletoe, which are anticancer molecules, as γ-thionins (another name for plant defensins). The person skilled in the art would understand that such prior art does not relate to plant defensins (γ-thionins) but instead to the structurally and functionally distinct α-/β-thionins.

Reports of Plant Defensins with Antiproliferative Activity on Human Cancer Cells Since 2004, some isolated reports have suggested that plant defensin(-like) proteins could also display in vitro antiproliferative activity against various human tumour cell lines (with differing potencies) (see, for example, Wong and Ng (2005), Ngai and Ng (2005), Ma et al. (2009) and Lin et al. (2009)). These proteins have largely been isolated from leguminous plants (e.g. beans). The assignment of these proteins lathe plant defensin class was based on their estimated molecular mass (~5 kDa) and in some cases, on limited N-terminal amino acid similarities to known defensin sequences. However, the proteins as disclosed in these references lack the strictly conserved cysteine residues and cysteine spacings that define defensins. In addition, the proteins disclosed in such references are not Class II defensins, nor are they from the family Solanaceae.

A review of the literature indicates that the Capsicum chinese defensin (CcD1), also referred to as Cc-gth, was the only other Class II defensin of the Solanaceae family that has been previously implicated as having the potential to inhibit the viability of mammalian cells (Anaya-Lopez et al., 2006). It is reported that the transfection of an expression construct encoding a full-length sequence for CcD1 into the bovine endothelial cell line BE-E6E7 resulted in conditioned media that exhibited anti-proliferative effects on the human transformed cell line HeLa. There are a number of major flaws in the experimental design and interpretation of these data that make it impossible for the person skilled in the art to draw a valid conclusion from the described studies as to whether CcD1 exhibits anti-proliferative activity. These include: (i) although mRNA for CcD1 was suggested in the transfected cells, no evidence was provided to demonstrate that the CcD1 protein was actually expressed in the conditioned media, (ii) the use of the full-length open-reading frame of CcD1 rather, than the mature coding domain would require the processing of the expressed precursor by removal of the CTPP domain to produce an "active" defensin—this was not demonstrated, (iii) the process of transfection can result in changes to a cell and the control for the transfection experiment was not adequate in that untransfected cells were used rather than the correct control of vector alone transfected cells, (iv) the use of conditioned media rather than purified CcD1 protein could influence the experimental readout as components of the media or other secreted molecules from the transfected cells may themselves, or in combination with CcD1, have anti-proliferative activity, (v) the expression levels of CcD1 mRNA in the various transfected endothelial cell populations (Anaya-Lopez et al., 2006, FIG. 2) do not correlate with the proposed anti-proliferative activity of the CcD1 transfected cell conditioned media (Anaya-Lopez et al., 2006, FIG. 4) as there is no statistically significant difference between the observed anti-proliferative responses mediated by the different conditioned media samples. It should also be noted that these deficiencies in the experimental design and interpretation were expressly acknowledged in an independently published paper by the same authors in 2008 (Loeza-Angeles et al., 2008). Based on these observations, it would be impossible for the person skilled in the art to interpret from Anaya-Lopez et al. (2006) that CcD1 has any anti-proliferative activity against mammalian cells.

The inventors have previously disclosed in International Patent Publication No. WO 02/063011 certain novel defensins and their use in inducing resistance in plants or parts of plants to pathogen infestation. The entire contents of WO 02/063011 are incorporated herein by reference.

As a result of follow up studies into plant defensins, the inventors have also previously disclosed in International Patent Publication No. WO 2011/160174 that Class II defensins from the Solanaceae plant family have potent cytotoxic properties. These significant findings described a novel and important way in which proliferative diseases may be prevented and treated. The entire contents of WO 2011/160174 are incorporated herein by reference.

As a result of yet further studies into plant defensins, it has been determined that a previously undisclosed Class II defensin from the Solanaceae plant family has potent cytotoxic properties that are surprisingly coupled with a very high IC$_{50}$ and hence a very high degree of specificity for tumour cells, as opposed to normal, healthy cells. Accordingly, these findings provide for vastly improved compositions and methods for the prevention and treatment of proliferative diseases such as cancer, as well as associated systems and kits. Such compositions, methods, systems and kits provide a hitherto unseen degree of specific targeting against tumour cells versus normal, healthy cells, and therefore minimize side effects. Such compositions also allow for much higher safe doses of treatment, thereby facilitating a much improved degree of efficacy in treatment.

SUMMARY OF THE INVENTION

In a first aspect of the present invention, there is provided a plant defensin.

In a second aspect of the present invention, there is provided a nucleic acid encoding the plant defensin of the first aspect.

In a third aspect of the present invention, there is provided a vector comprising the nucleic acid of the second aspect.

In a fourth aspect of the present invention, there is provided a host cell comprising the vector of the third aspect.

In a fifth aspect of the present invention, there is provided an expression product produced by the host cell of the fourth aspect.

In a sixth aspect of the present invention, there is provided a pharmaceutical composition for use in preventing or treating a proliferative disease, wherein the pharmaceutical composition comprises the plant defensin of the first aspect, the nucleic acid of the second aspect, the vector of the third aspect, the host cell of the fourth aspect or the expression product of the fifth aspect, together with a pharmaceutically acceptable carrier, diluent or excipient.

In a seventh aspect of the present invention, there is provided a method for preventing or treating a proliferative disease, wherein the method comprises administering to a subject a therapeutically effective amount of the plant defensin of the first aspect, the nucleic acid of the second aspect, the vector of the third aspect, the host cell of the fourth aspect, the expression product of the fifth aspect or the pharmaceutical composition of the sixth aspect, thereby preventing or treating the proliferative disease.

In an eighth aspect of the present invention, there is provided use of the plant defensin of the first aspect, the nucleic acid of the second aspect, the vector of the third aspect, the host cell of the fourth aspect, the expression product of the fifth aspect or the pharmaceutical composition of the sixth aspect in the preparation of a medicament for preventing or treating a proliferative disease.

In a ninth aspect of the present invention, there is provided a kit for preventing or treating a proliferative disease, wherein the kit comprises a therapeutically effective amount of the plant defensin of the first aspect, the nucleic acid of the second aspect, the vector of the third aspect, the host cell of the fourth aspect, the expression product of the fifth aspect or the pharmaceutical composition of the sixth aspect.

In a tenth aspect of the present invention, there is provided use of the kit of the ninth aspect for preventing or treating a proliferative disease, wherein the therapeutically effective amount of the plant defensin of the first aspect, the nucleic acid of the second aspect, the vector of the third aspect, the host cell of the fourth aspect, the expression product of the fifth aspect or the pharmaceutical composition of the sixth aspect is administered to a subject, thereby preventing or treating the proliferative disease.

In an eleventh aspect of the present invention, there is provided a method for producing a plant defensin with reduced haemolytic activity, wherein the method comprises introducing into the plant defensin at least one alanine residue at or near the N-terminal of the defensin.

In a twelfth aspect of the present invention, there is provided a plant defensin with reduced haemolytic activity produced by the method according to the eleventh aspect.

Definitions

The term "derivable" includes, and may be used interchangeably with, the terms "obtainable" and "isolatable". Compositions or other matter of the present invention that is "derivable", "obtainable" or "isolatable" from a particular source or process include not only compositions or other matter derived, obtained or isolated from that source or process, but also the same compositions or matter however sourced or produced.

As used herein the term "polypeptide" means a polymer made up of amino acids linked together by peptide bonds, and includes fragments or analogues thereof. The terms "polypeptide", "protein" and "amino acid" are used interchangeably herein, although for the purposes of the present invention a "polypeptide" may constitute a portion of a full length protein.

The term "nucleic acid" as used herein refers to a single- or double-stranded polymer of deoxyribonucleotide, ribonucleotide bases or known analogues of natural nucleotides, or mixtures thereof. The term includes reference to the specified sequence as well as to the sequence complementary thereto, unless otherwise indicated. The terms "nucleic acid", "polynucleotide" and "nucleotide sequence" are used herein interchangeably. It will be understood that "5' end" as used herein in relation to a nucleic acid corresponds to the N-terminus of the encoded polypeptide and "3' end" corresponds to the C-terminus of the encoded polypeptide.

The term "purified" means that the material in question has been removed from its natural environment or host, and associated impurities reduced or eliminated such that the molecule in question is the predominant species present. The term "purified" therefore means that an object species is the predominant species present (ie., on a molar basis it is more abundant than any other individual species in the composition), and preferably a substantially purified fraction is a composition wherein the object species comprises at least about 30 percent (on a molar basis) of all macromolecular species present. Generally, a substantially pure composition will comprise more than about 80 to 90 percent of all macromolecular species present in the composition. Most preferably, the object species is purified to essential homogeneity (contaminant species cannot be detected in the composition by conventional detection methods) wherein the composition consists essentially of a single macromolecular species. The terms "purified" and "isolated" may be used interchangeably. Purity and homogeneity are typically determined using analytical chemistry techniques such as polyacrylamide gel electrophoresis or high performance liquid chromatography. A protein or nucleic acid that is the predominant species present in a preparation is substantially purified. The term "purified" in some embodiments denotes that a protein or nucleic acid gives rise to essentially one band in an electrophoretic gel.

The term "fragment" refers to a polypeptide or nucleic acid that encodes a constituent or is a constituent of a polypeptide or nucleic acid of the invention thereof. Typically the fragment possesses qualitative biological activity in common with the polypeptide or nucleic acid of which it is a constituent. A peptide fragment may be between about 5 to about 150 amino acids in length, between about 5 to about 100 amino acids in length, between about 5 to about 50 amino acids in length, or between about 5 to about 25 amino acids in length. Alternatively, the peptide fragment may be between about 5 to about 15 amino acids in length. The term "fragment" therefore includes a polypeptide that is a constituent of a full-length plant defensin polypeptide and possesses qualitative biological activity in common with a full-length plant defensin polypeptide. A fragment may be derived from a full-length plant defensin polypeptide or alternatively may be synthesised by some other means, for example chemical synthesis.

The term "fragment" may also refer to a nucleic acid that encodes a constituent or is a constituent of a polynucleotide of the invention. Fragments of a nucleic acid do not necessarily need to encode polypeptides which retain biological activity. Rather the fragment may, for example, be useful as a hybridization probe or PCR primer. The fragment may be derived from a polynucleotide of the invention or alternatively may be synthesized by some other means, for example chemical synthesis. Nucleic acids of the present invention and fragments thereof may also be used in the production of antisense molecules using techniques known to those skilled in the art.

The term "recombinant" when used with reference, for example, to a cell, nucleic acid, protein or vector, indicates that the cell, nucleic acid, protein or vector has been modified by the introduction of a heterologous nucleic acid or protein or by the alteration of a native nucleic acid or protein, or that the cell is derived from a cell so modified. Accordingly, "recombinant" cells express genes that are not found within the native (non-recombinant) form of the cell or express native genes that are otherwise abnormally expressed, under expressed or not expressed at all. By the term "recombinant nucleic acid" is meant a nucleic acid, originally formed in vitro, in general, by the manipulation of a nucleic acid, for example, using polymerases and endonucleases, in a form not normally found in nature. In this manner, operable linkage of different sequences is achieved. Thus an isolated nucleic acid, in a linear form, or an expression vector formed in vitro by ligating DNA molecules that are not normally joined, are both considered "recombinant" for the purposes of this invention. It is understood that once a recombinant nucleic acid is made and reintroduced into a host cell or organism, it will replicate non-recombinantly, i.e., using the in vivo cellular machinery of the host cell rather than in vitro manipulations. However, such nucleic acids, once produced recombinantly, although subsequently replicated non-recombinantly, are still considered recombinant for the purposes of the invention. Similarly, a "recombinant protein" is a protein made using recombinant techniques, i.e., through the expression of a recombinant nucleic acid as depicted above.

The terms "identical" or percent "identity" in the context of two or more polypeptide (or nucleic acid) sequences, refer to two or more sequences or sub-sequences that are the same or have a specified percentage of amino acid residues (or nucleotides) that are the same over a specified region, when compared and aligned for maximum correspondence over a comparison window or designated region, as measured using sequence comparison algorithms, or by manual alignment and visual inspection, such techniques being well known to the person skilled in the art.

As used herein the term "treatment", refers to any and all uses which remedy a disease state or symptoms, prevent the establishment of disease, or otherwise prevent, hinder, retard, ameliorate or reverse the progression of disease or other undesirable symptoms in any way whatsoever.

Unless defined otherwise, all technical and scientific terms used herein have the same meaning as commonly understood by one of ordinary skill in the art (e.g. in cell biology, chemistry, molecular biology and cell culture). Standard techniques used for molecular and biochemical methods can be found in Sambrook et al., Molecular Cloning: A Laboratory Manual, 3$^{rd}$ ed. (2001) Cold Spring Harbor Laboratory Press, Cold Spring Harbor, N.Y. and Ausubel et al., Short Protocols in Molecular Biology (1999) 4$^{th}$ Ed, John Wiley & Sons, Inc.—and the full version entitled Current Protocols in Molecular Biology).

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

Throughout this specification, reference to numerical values, unless stated otherwise, is to be taken as meaning "about" that numerical value. The term "about" is used to indicate that a value includes the inherent variation of error for the device and the method being employed to determine the value, or the variation that exists among the study subjects.

The reference to any prior art in this specification is not, and should not be taken as an acknowledgement or any form of suggestion that prior art forms part of the common general knowledge of the person skilled in the art.

The entire content of all publications, patents, patent applications and other material recited in this specification is incorporated herein by reference.

BRIEF DESCRIPTION OF THE SEQUENCE LISTING

SEQ ID NO: 1 is an exemplary full length amino acid sequence for the plant defensin NoD173, with SEQ ID NO: 2 being the corresponding nucleic acid sequence.

SEQ ID NO: 3 is an exemplary amino acid sequence for the mature domain of the plant defensin NoD173, with SEQ ID NO: 4 being the corresponding nucleic acid sequence.

SEQ ID NO: 5 is an exemplary amino acid sequence for a recombinantly altered mature domain of the plant defensin NoD173, having an additional alanine residue at the N-terminal, with SEQ ID NO: 6 being the corresponding nucleic acid sequence.

SEQ ID NO: 7 is the forward primer FLOR1 used for PCR amplification of NoD173 from genomic DNA, with SEQ ID NO: 8 being the reverse primer.

SEQ ID NO: 9 is the forward primer NoD173fw used for Cloning of NoD173 into pPIC9 for expression in *Pichia pastoris*, with SEQ ID NO: 10 being the reverse primer.

BRIEF DESCRIPTION OF THE FIGURES

The present invention will now be described, by way of example only, with reference to the following figures.

FIG. 2A-B are amino acid sequence alignments of the mature domains of various Class I and Class II plant defensins. Identity or homology is indicated by black-or grey-boxed residues, respectively ((A) shaded version). Conserved disulfide bonds are shown as solid lines. (B) The same information is shown as an unshaded version.

DETAILED DESCRIPTION OF THE INVENTION

The inventors have isolated and characterized a previously undisclosed Class II defensin from the Solanaceae plant family that has potent cytotoxic properties and which surprisingly has a very high IC$_{50}$. This newly disclosed plant defensin has a very high degree of specificity for killing tumour cells, as opposed to normal, healthy cells. Accordingly, these findings provide for vastly improved compositions and methods for the prevention and treatment of proliferative diseases such as cancer, as well as associated systems and kits. Such compositions, methods, systems and kits provide a hitherto unseen degree of specific targeting against tumour cells versus normal, healthy cells, and therefore minimize side effects. Such compositions also allow for much higher safe doses of treatment, thereby facilitating a much improved degree of efficacy in treatment. These significant findings describe a novel and important way in which proliferative diseases may be prevented and treated. Accordingly, these findings provide for compositions and methods for the prevention or treatment of proliferative diseases such as cancer, as well as associated uses, systems and kits.

NoD173 is a plant defensin isolated from floral tissue of *Nicotiana occidentalis* ssp *obliqua*. The amino acid and coding sequences of NoD173 are disclosed herein. The ability to produce large quantities of active defensins such as NoD173 is of fundamental importance when considering potential use as a therapeutic in a clinical setting. The purification of the required large amounts of NoD173 from its natural source (flowers of the tobacco *N. occidentalis*) is not feasible, necessitating the production of active recombinant protein. A *Pichia pastoris* expression system combined with a defined protein purification approach has been successfully established to produce high levels of pure active recombinant NoD173.

Figure 3:
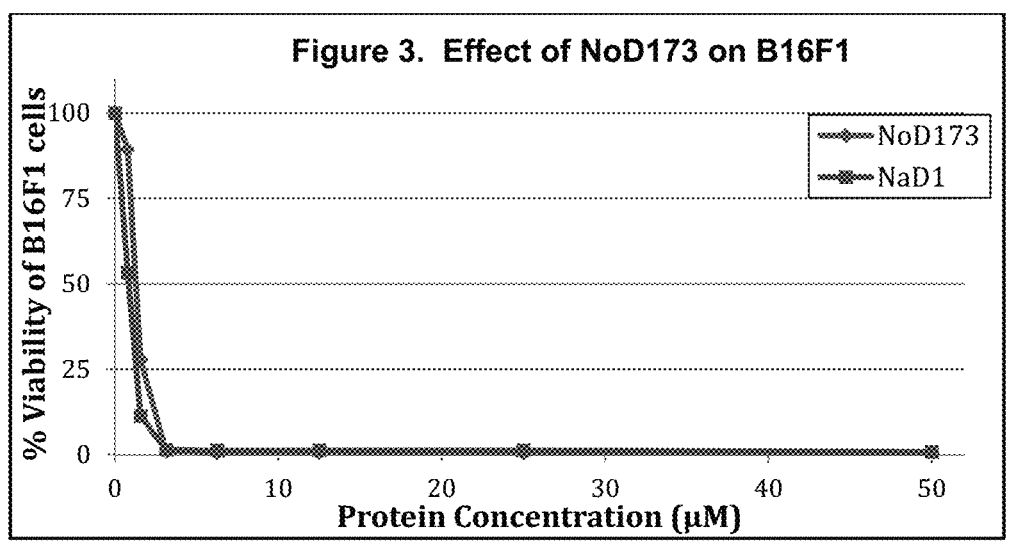
FIG. 3: shows that NoD173 kills mouse melanoma B16F1 cells with similar efficiency to NaD1 ($IC_{50}$ 1.5 μM) as indicated by in vitro cell viability assays.
Figure 4:
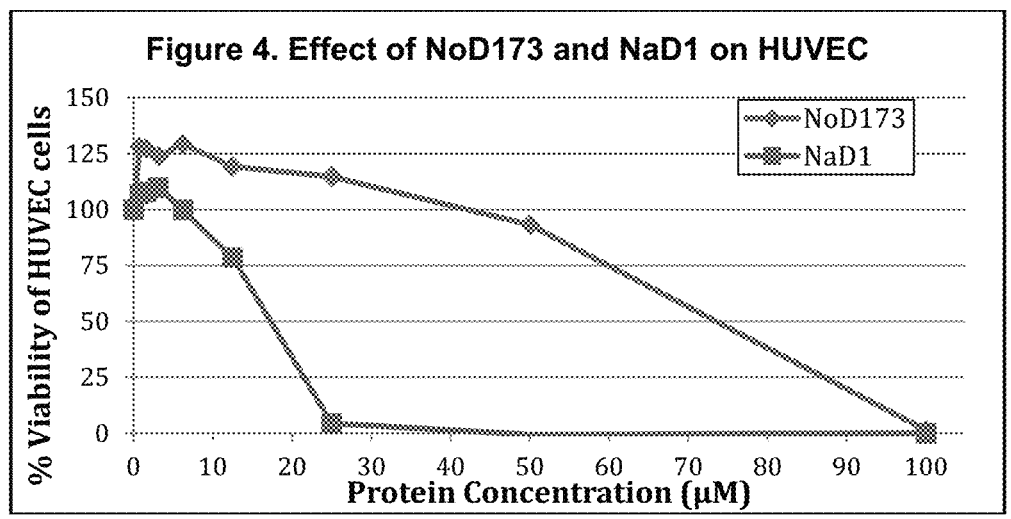
FIG. 4: shows that NoD173 is highly selective for the killing of tumour cells compared to normal cells. The $IC_{50}$ of NoD173 for normal human umbilical vein endothelial cells (HUVEC) is shown as 75 μM, indicating that normal cells are 50-fold more resistant to being killed than B16F1 tumour cells. NoD173 is shown to kill HUVEC only at a much higher concentration when compared with another model class II defensin, NaD1, which kills HUVEC at an $IC_{50}$ of 15 μM.

The inventors have shown that NoD173 selectively kills a number of different tumour cells. For example, NoD173 has been shown to kill mouse melanoma B16F1 cells with similar efficiency to NaD1 (IC$_{50}$ 1.5 µM) as indicated by in vitro cell viability assays (FIG. 3). Furthermore, NoD173 is highly selective for the killing of tumour cells over normal cells. The IC$_{50}$ of NoD173 for normal human cells umbilical vein endothelial cells (HUVEC) is 75 µM, indicating normal cells are 50-fold more resistant to being killed than B16F1 (FIG. 4). The significant improvement of NoD173 over other class II defensins is also clearly evident when compared to NaD1, which kills HUVEC at a much lower concentration (IC$_{50}$ of 15 µM) (FIG. 4).

In addition, toxicity studies in mice administered NoD173 showed no toxicity when NoD173 was delivered subcutaneously or intratumourly at concentrations of up to 5 mg/kg.

Figure 5:
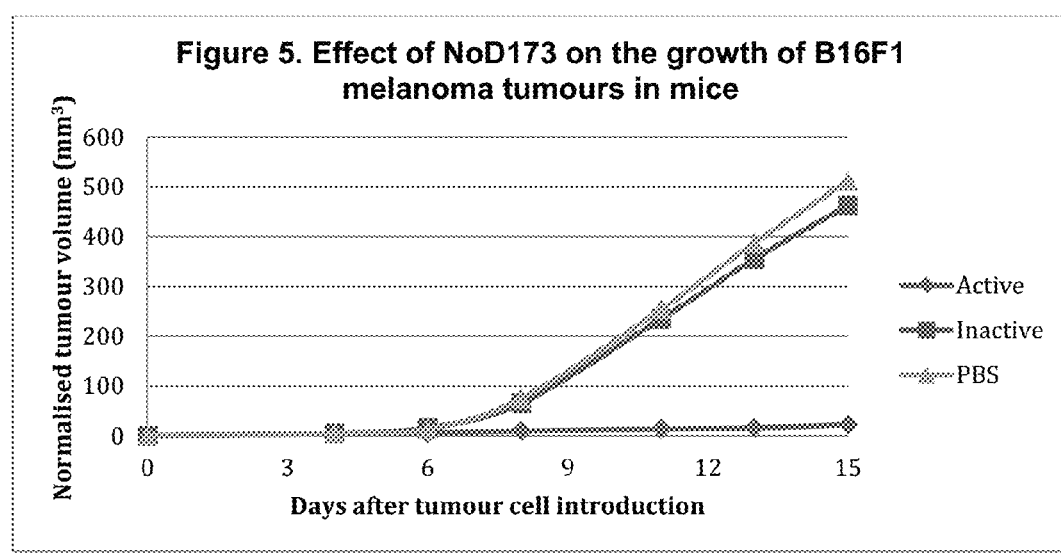
FIG. 5: shows that the intra-tumour injection of 10 mm³ established subcutaneous tumours with NoD173 (active) over two weeks dramatically reduced tumour growth when compared to reduced and alkylated NoD173 (inactive) and vehicle control (Phosphate-buffered saline, PBS).

NoD173 has also been shown to reduce the growth of aggressive solid tumours in vivo. For example, after the intra-tumour injection of mice, causing the establishment of subcutaneous tumours, subsequent administration with NoD173 over two weeks dramatically reduced tumour growth when compared to inactive NoD173 (reduced and alkylated) and a vehicle control (Phosphate-buffered saline, PBS) (FIG. 5). These data indicate that NoD173 represents a class II defensin with significant selectivity improvements over other class II defensins such as NaD1.

Figure 6:
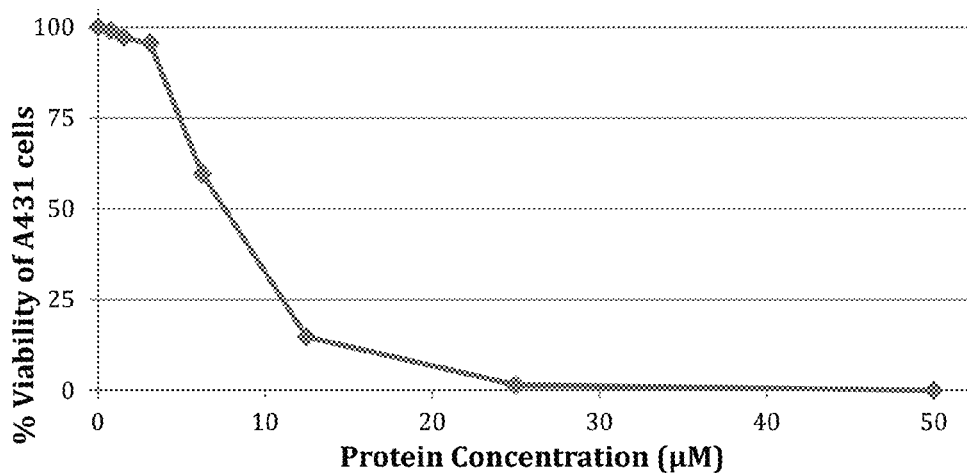
FIG. 6: shows the effect of NoD173 on (A) the human squamous cell carcinoma cell line (A431) and (B) the human BCC cell line (CRL-7762) using MTT cell viability assays. NoD173 killed CRL-7762 and A431 at low µM concentrations (IC$_{50}$ 15 µM and 10 µM, respectively) indicating that both of these non-melanoma skin cancers are sensitive to killing by NoD173.
Figure 6:
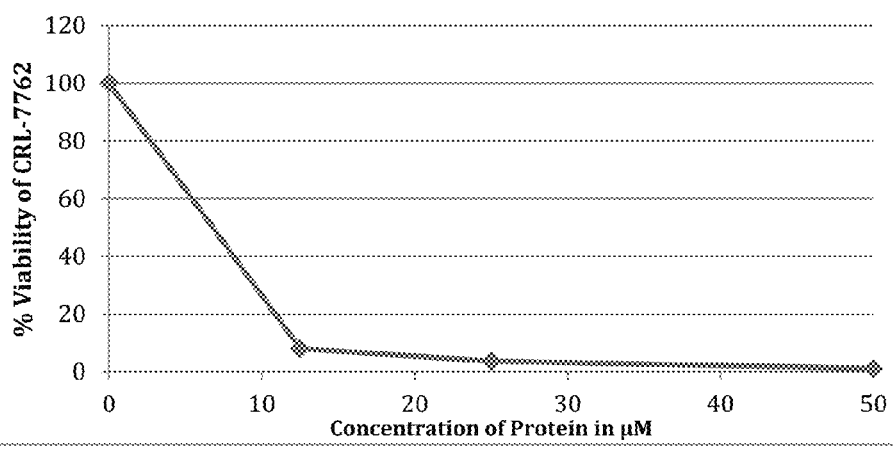

NoD173 has further been shown to provide effective treatment for basal cell and squamous cell carcinoma. The susceptibility of the human squamous cell carcinoma cell line (A431) and the human BCC cell line (CRL-7762) to NoD173 was assessed in vitro using MTT cell viability assays. NoD173 killed CRL-7762 and A431 at low µM concentrations (IC$_{50}$ 15 µM and 10 µM, respectively) indicating that both of these non-melanoma skin cancers are sensitive to killing by NoD173 (FIGS. 6A and B).

Plant Defensins for use in Preventing or Treating a Proliferative Disease

The present invention provides novel plant defensins. The novel plant defensins are useful in preventing or treating a proliferative disease.

In preferred embodiments, the plant defensin is NoD173 (SEQ ID NOs: 1, 3 or 5), being a plant gamma-thionin having at least eight canonical cysteine residues which form disulfide bonds in the configuration: Cys$_I$-Cys$_{VIII}$, Cys$_{II}$-Cys$_{IV}$, Cys$_{III}$-Cys$_{VI}$ and Cys$_V$-Cys$_{VII}$.

The plant defensin is also a Class II plant defensin with or having previously had a C-terminal prodomain or propeptide (CTPP), and being derived or derivable from Solanaceae.

In some embodiments, the plant defensin comprises the amino acid sequence set forth as SEQ ID NOs: 1, 3 or 5 or a fragment thereof.

In yet other embodiments, the plant defensin comprises an amino acid sequence that is 95%, 90%, 85%, 80%, 75%, 70%, 65% or 60% identical to the amino acid sequence set forth as SEQ ID NOs:1, 3 or 5 or a fragment thereof.

In still other embodiments, the plant defensin comprises an amino acid sequence that is 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61%, 60%, 59%, 58%, 57%, 56%, 55%, 54%, 53%, 52%, 51%, 50%, 49%, 48%, 47%, 46%, 45%, 44%, 43%, 42%, 41%, 40%, 39%, 38%, 37%, 36%, 35%, 34%, 33%, 32%, 31%, 30%, 29%, 28%, 27%, 26%, 25%, 24%, 23%, 22%, 21%, 20%, 19%, 18%, 17%, 16%, 15%, 14%, 13%, 12%, 11%, 10%, 9%, 8%, 7%, 6%, 5%, 4%, 3%, 2% or 1% identical to the amino acid sequence set forth as SEQ ID NOs:1, 3 or 5 or a fragment thereof.

In some embodiments, the plant defensin comprises an amino acid sequence that is 85% identical to the amino acid sequence set forth as SEQ ID NOs:1, 3 or 5 or a fragment thereof.

In particular embodiments, the plant defensin is derived or derivable from *Nicotiana Occidentalis*.

In particular embodiments, the plant defensin is derived or derivable from *Nicotiana Occidentalis* spp *obliqua*.

In some embodiments, the plant defensin may be a fragment of any amino acid sequence or a fragment or complement of any nucleic acid sequence disclosed herein.

In particular embodiments, the fragment may comprise a mature domain.

In preferred embodiments, the amino acid sequence of the mature domain is set forth as SEQ ID NO: 3.

In some embodiments, the plant defensin may be an isolated, purified or recombinant plant defensin.

In particular embodiments, the recombinant plant defensin has an additional alanine residue at or near the N-terminal end.

In preferred embodiments, the recombinant plant defensin has reduced haemolytic activity.

In particularly preferred embodiments, the recombinant plant defensin comprises the amino acid sequence set forth as SEQ ID NO: 5, or a fragment thereof.

In particular embodiments, the plant defensin comprises an amino acid sequence derived from the following genomic clone, wherein the ER amino acid signal sequence is shown in italics, the C-terminal propeptide is shown in underline, and the intronic nucleotide sequence is shown with nucleotides in lowercase. The uppercase amino acid sequence shown without italics or underline is the mature protein domain (SEQ ID NO: 3).

```
           10        20        30        40        50
    ....|....|....|....|....|....|....|....|....|....|
    ATGGCTCGCTCCTTGTGCTTCATGGGATTTGCTATCTTGGCAATGATGCT
     M   A   R   S   L   C   F   M   G   F   A   I   L   A   M   M   L 60        70        80        90       100
    ....|....|....|....|....|....|....|....|....|....|
    CTTTGTTGCCTATggtttgtctccatttattcctctaaaacccattaaa
     F   V   A   Y 110       120       130       140       150
    ....|....|....|....|....|....|....|....|....|....|
    ataataaaagctatgactggtttagttatcatgatgaacatcaagttaca 160       170       180       190       200
    ....|....|....|....|....|....|....|....|....|....|
    cttcttatgatttgtctagtaattattcaagtgtggttatcattttgatg 210       220       230       240       250
    ....|....|....|....|....|....|....|....|....|....|
    tatttgttgttaaaacgacgaattaatctatagtatacgtctgatagctt 260       270       280       290       300
    ....|....|....|....|....|....|....|....|....|....|
    tgaaaaatcctgaaaaatatgtgttcgcattagttcttccaaaatagtat 310       320       330       340       350
    ....|....|....|....|....|....|....|....|....|....|
    atagggcggtatattttttagggtatgatgtcgatctatattacatccc 360       370       380       390       400
    ....|....|....|....|....|....|....|....|....|....|
    ttggaatgcggcctgattttctggaccctttatgcactggactgcccta 410       420       430       440       450
    ....|....|....|....|....|....|....|....|....|....|
    tatatatacacacatgtatgtatgtttaataaccttgaatcctgttttt 460       470       480       490       500
    ....|....|....|....|....|....|....|....|....|....|
    tattgtttctttcaattctatcttttcttttgttctaacattggtaagta 510       520       530       540       550
    ....|....|....|....|....|....|....|....|....|....|
    cttgtgaatgattgtaGAGGTGCAAGCTAGACAATGCAAAGCAGAAAGCA
                    E   V   Q   A   R   Q   C   K   A   E   S 560       570       580       590       600
    ....|....|....|....|....|....|....|....|....|....|
    ATACATTCACTGGAATATGCATTGCCAAACCACCATGCAGACAAGCTTGT
     N   T   F   T   G   I   C   I   A   K   P   P   C   R   Q   A   C 610       620       630       640       650
    ....|....|....|....|....|....|....|....|....|....|
    ATCCGTGAGAAATTTACTGATGGTCATTGTAGCAAAGTCCTCAGAAGGTG
     I   R   E   K   F   T   D   G   H   C   S   K   V   L   R   R   C 660       670       680       690       700
    ....|....|....|....|....|....|....|....|....|....|
    TCTATGCACTAAGCGATGTGTGTTTGATGAGAAGATGATCGAAACAGGAG
     L   C   T   K   R   C   V   F   D   E   K   M   I   E   T   G 710       720       730       740       750
    ....|....|....|....|....|....|....|....|....|....|
    CTGAAACCTTAGCTGAGGAAGCAAAAACTTTTGCTGCAGCTTTGCTTGAA
     A   E   T   L   A   E   E   A   K   T   F   A   A   A   L   L   E 760       770
    ....|....|....|....|.
    GAAGAGATAATGGATAACTGA
     E   E   I   M   D   N   *
```

Polynucleotides

In embodiments where the compositions of the present invention comprise polypeptides, the present invention also provides nucleic acids encoding such polypeptides, or fragments or complements thereof. Such nucleic acids may be naturally occurring or may be synthetic or recombinant.

In some embodiments, the nucleic acids may be operably linked to one or more promoters. In particular embodiments, the nucleic acids may encode polypeptides that prevent or treat proliferative diseases.

In some embodiments, the plant defensin is therefore provided in the form of a nucleic acid. In some embodiments, the plant defensin nucleic acid encodes the amino acid sequence set forth as SEQ ID NOs: 1, 3 or 5 or a fragment thereof. In yet other embodiments, the plant defensin nucleic acid comprises the nucleotide sequence set forth as SEQ ID NOs: 2, 4 or 6 or a fragment or complement thereof.

In yet other embodiments, the plant defensin nucleic acid comprises a nucleotide sequence that is 95%, 90%, 85%, 80%, 75%, 70%, 65% or 60% identical to the nucleotide sequence set forth as SEQ ID NOs: 2, 4 or 6 or a fragment or complement thereof.

In still other embodiments, the plant defensin nucleic acid comprises a nucleotide sequence that is 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61%, 60%, 59%, 58%, 57%, 56%, 55%, 54%, 53%, 52%, 51%, 50%, 49%, 48%, 47%, 46%, 45%, 44%, 43%, 42%, 41%, 40%, 39%, 38%, 37%; 36%, 35%, 34%, 33%, 32%, 31%, 30%, 29%, 28%, 27%, 26%, 25%, 24%, 23%, 22%, 21%, 20%, 19%, 18%, 17%, 16%, 15%, 14%, 13%, 12%, 11%, 10%, 9%, 8%, 7%, 6%, 5%, 4%, 3%, 2% or 1% identical to the nucleotide sequence set forth as SEQ ID NOs: 2, 4 or 6 or a fragment or complement thereof.

In some embodiments, the plant defensin comprises a nucleotide sequence that is 85%, identical to the nucleotide sequence set forth as SEQ ID NOs: 2, 4 or 6 or a fragment or complement thereof.

Vectors, Host Cells and Expression Products

The present invention also provides vectors comprising the nucleic acids as set forth herein. The vector may be a plasmid vector, a viral vector, or any other suitable vehicle adapted for the insertion of foreign sequences, its introduction into cells and the expression of the introduced sequences. The vector may be a eukaryotic expression vector and may include expression control and processing sequences such as a promoter, an enhancer, ribosome binding sites, polyadenylation signals and transcription termination sequences. In preferred embodiments, the vector comprises one or more nucleic acids operably encoding any one or more of the plant defensins set forth herein.

The present invention further provides host cells comprising the vectors as set forth herein. Typically, a host cell is transformed, transfected or transduced with a vector, for example, by using electroporation followed by subsequent selection of transformed, transfected or transduced cells on selective media. The resulting heterologous nucleic acid sequences in the form of vectors and nucleic acids inserted therein may be maintained extrachromosomally or may be introduced into the host cell genome by homologous recombination. Methods for such cellular transformation, transfection or transduction are well known to those of skill in the art. Guidance may be obtained, for example, from standard texts such as Sambrook et al., *Molecular Cloning: A Laboratory Manual,* Cold Spring Harbor, New York, 1989 and Ausubel et al., *Current Protocols in Molecular Biology,* Greene Publ. Assoc. and Wiley-Intersciences, 1992.

The present invention moreover provides expression products of the host cells as set forth herein. In some embodiments, the expression product may be polypeptides that prevent or treat proliferative diseases. In preferred embodiments, the expression product is any one or more of the plant defensins disclosed herein.

Compositions

The present invention also provides pharmaceutical compositions for use in preventing or treating proliferative diseases, wherein the pharmaceutical compositions comprise a plant defensin, a nucleic acid, a vector, a host cell or an expression product as disclosed herein, together with a pharmaceutically acceptable carrier, diluent or excipient.

Compositions of the present invention may therefore be administered therapeutically. In such applications, compositions may be administered to a subject already suffering from a condition, in an amount sufficient to cure or at least partially arrest the condition and any complications. The quantity of the composition should be sufficient to effectively treat the patient. Compositions may be prepared according to methods which are known to those of ordinary skill in the art and accordingly may include a cosmetically or pharmaceutically acceptable carrier, excipient or diluent. Methods for preparing administrable compositions are apparent to those skilled in the art, and are described in more detail in, for example, Remington's Pharmaceutical Science, 15th ed., Mack Publishing Company, Easton, Pa., incorporated by reference herein.

The composition may incorporate any suitable surfactant such as an anionic, cationic or non-ionic surfactant such as sorbitan esters or polyoxyethylene derivatives thereof. Suspending agents such as natural gums, cellulose derivatives or inorganic materials such as silicaceous silicas, and other ingredients such as lanolin, may also be included.

The compositions may also be administered in the form of liposomes. Liposomes may be derived from phospholipids or other lipid substances, and may be formed by mono-or multi-lamellar hydrated liquid crystals dispersed in an aqueous medium. Any non-toxic, physiologically acceptable and metabolisable lipid capable of forming liposomes may be used. The compositions in liposome form may contain stabilisers, preservatives and excipients. Preferred lipids include phospholipids and phosphatidyl cholines (lecithins), both natural and synthetic. Methods for producing liposomes are known in the art, and in this regard specific reference is made to: Prescott, Ed., Methods in Cell Biology, Volume XIV, Academic Press, New York, N.Y. (1976), p. 33 et seq., the contents of which are incorporated herein by reference.

In some embodiments, the composition may be in the form of a tablet, liquid, lotion, cream, gel, paste or emulsion.

Dosages

The "therapeutically effective" dose level for any particular patient will depend upon a variety of factors including the condition being treated and the severity of the condition, the activity of the compound or agent employed, the composition employed, the age, body weight, general health, sex and diet of the patient, the time of administration, the route of administration, the rate of sequestration of the plant defensin or composition, the duration of the treatment, and any drugs used in combination or coincidental with the treatment, together with other related factors well known in the art. One skilled in the art would therefore be able, by routine experimentation, to determine an effective, non-toxic amount of the plant defensin or composition which would be required to treat applicable conditions.

Typically, in therapeutic applications, the treatment would be for the duration of the disease state.

Further, it will be apparent to one of ordinary skill in the art that the optimal quantity and spacing of individual dosages of the composition will be determined by the nature and extent of the condition being treated, the form, route and site of administration, and the nature of the particular individual being treated. Also, such optimum conditions can be determined by conventional techniques.

It will also be apparent to one of ordinary skill in the art that the optimal course of treatment, such as the number of doses of the composition given per day for a defined number of days, can be ascertained by those skilled in the art using conventional course of treatment determination tests.

In terms of weight, a therapeutically effective dosage of a composition for administration to a patient is expected to be in the range of about 0.01 mg to about 150 mg per kg body weight per 24 hours; typically, about 0.1 mg to about 150 mg per kg body weight per 24 hours; about 0.1 mg to about 100 mg per kg body weight per 24 hours; about 0.5 mg to about 100 mg per kg body weight per 24 hours; or about 1.0 mg to about 100 mg per kg body weight per 24 hours. More typically, an effective dose range is expected to be in the range of about 5 mg to about 50 mg per kg body weight per 24 hours.

Alternatively, an effective dosage may be up to about 5000 mg/m$^2$. Generally, an effective dosage is expected to be in the range of about 10 to about 5000 mg/m$^2$, typically about 10 to about 2500 mg/m$^2$, about 25 to about 2000 mg/m$^2$, about 50 to about 1500 mg/m$^2$, about 50 to about 1000 mg/m$^2$, or about 75 to about 600 mg/m$^2$.

Routes of Administration

The compositions of the present invention can be administered by standard routes. In general, the compositions may be administered by the parenteral (e.g., intravenous, intraspinal, subcutaneous or intramuscular), oral or topical route.

In other embodiments, the compositions may be administered by other enteral/enteric routes, such as rectal, sublingual or sublabial, or via the central nervous system, such as through epidural, intracerebral or intracerebroventricular routes. Other locations for administration may include via epicutaneous, transdermal, intradermal, nasal, intraarterial, intracardiac, intraosseus, intrathecal, intraperitoneal, intravesical, intravitreal, intracavernous, intravaginal or intrauterine routes.

Carriers, Excipients and Diluents

Carriers, excipients and diluents must be "acceptable" in terms of being compatible with the other ingredients of the composition, and not deleterious to the recipient thereof. Such carriers, excipients and diluents may be used for enhancing the integrity and half-life of the compositions of the present invention. These may also be used to enhance or protect the biological activities of the compositions of the present invention.

Examples of pharmaceutically acceptable carriers or diluents are demineralised or distilled water; saline solution; vegetable based oils such as peanut oil, safflower oil, olive oil, cottonseed oil, maize oil, sesame oils, arachis oil or coconut oil; silicone oils, including polysiloxanes, such as methyl polysiloxane, phenyl polysiloxane and methylphenyl polysolpoxane; volatile silicones; mineral oils such as liquid paraffin, soft paraffin or squalane; cellulose derivatives such as methyl cellulose, ethyl cellulose, carboxymethylcellulose, sodium carboxymethylcellulose or hydroxypropylmethylcellulose; lower alkanols, for example ethanol or isopropanol; lower aralkanols; lower polyalkylene glycols or lower alkylene glycols, for example polyethylene glycol, polypropylene glycol, ethylene glycol, propylene glycol, 1,3-butylene glycol or glycerin; fatty acid esters such as isopropyl palmitate, isopropyl myristate or ethyl oleate; polyvinylpyrolidone; agar; gum tragacanth or gum acacia, and petroleum jelly. Typically, the carrier or carriers will form from 10% to 99.9% by weight of the compositions.

The compositions of the invention may be in a form suitable for administration by injection, in the form of a formulation suitable for oral ingestion (such as capsules, tablets, caplets, elixirs, for example), in the form of an ointment, cream or lotion suitable for topical administration, in an aerosol form suitable for administration by inhalation, such as by intranasal inhalation or oral inhalation, in a form suitable for parenteral administration, that is, subcutaneous, intramuscular or intravenous injection.

For administration as an injectable solution or suspension, non-toxic acceptable diluents or carriers can include Ringer's solution, isotonic saline, phosphate buffered saline, ethanol and 1,2 propylene glycol.

Methods for Preventing or Treating Proliferative Diseases

The present invention provides methods for preventing or treating a proliferative disease, wherein the methods comprise administering to a subject a therapeutically effective amount of a plant defensin, a nucleic acid, a vector, a host cell, an expression product or a pharmaceutical composition as disclosed herein, thereby preventing or treating the proliferative disease.

The present invention also provides use of plant defensins, nucleic acids, vectors, host cells and expression products as herein disclosed in the preparation of medicaments for preventing or treating a proliferative disease.

In some embodiments, the proliferative disease may be a cell proliferative disease selected from the group comprising an angiogenic disease, a metastatic disease, a tumourigenic disease, a neoplastic disease and cancer.

In some embodiments, the proliferative disease may be cancer. In particular embodiments, the cancer may be selected from the group comprising basal cell carcinoma, squamous cell carcinoma, actinic keratosis, bone cancer, bowel cancer, brain cancer, breast cancer, cervical cancer, leukemia, liver cancer, lung cancer, lymphoma, melanoma, ovarian cancer, pancreatic cancer, prostate cancer or thyroid cancer.

In other embodiments, the cancer may be selected from the group comprising acute lymphoblastic leukemia, actinic keratosis, acute myeloid leukemia, adrenocortical carcinoma, AIDS-related cancers, anal cancer, appendix cancer, astrocytoma, B-cell lymphoma, basal cell carcinoma, bile duct cancer, bladder cancer, bone cancer, bowel cancer, brainstem glioma, brain tumour, breast cancer, bronchial adenomas/carcinoids, Burkitt's lymphoma, carcinoid tumour, cerebral astrocytoma/malignant glioma, cervical cancer, childhood cancers, chronic lymphocytic leukemia, chronic myelogenous leukemia, chronic myeloproliferative disorders, colon cancer, cutaneous T-cell lymphoma, desmoplastic small round cell tumour, endometrial cancer, ependymoma, esophageal cancer, extracranial germ cell tumour, extragonadal germ cell tumour, extrahepatic bile duct cancer, eye cancer, intraocular melanoma/retinoblastoma, gallbladder cancer, gastric cancer, gastrointestinal carcinoid tumour, gastrointestinal stromal tumour (GIST), germ cell tumour, gestational trophoblastic tumour, glioma, gastric carcinoid, head and/or neck cancer, heart cancer, hepatocellular (liver) cancer, hypopharyngeal cancer, hypothalamic and visual pathway glioma, Kaposi sarcoma, kidney cancer, laryngeal cancer, leukemia (acute lymphoblastic/acute myeloid/chronic lymphocytic/chronic myelcigenous/hairy cell), lip and/or oral cavity cancer, liver cancer, non-small cell lung cancer, small cell lung cancer, lymphoma (AIDS-related/Burkitt/cutaneous T-Cell/Hodgkin/non-Hodgkin/primary central nervous system), macroglobulinemia, malignant fibrous histiocytoma of bone/osteosarcoma, medulloblastoma, melanoma, Merkel cell carcinoma, mesothelioma, metastatic squamous neck cancer, mouth cancer, multiple endocrine neoplasia syndrome, multiple myeloma/plasma cell neoplasm, mycosis fungoides, myelodysplastic syndromes, myelodysplastic/myeloproliferative diseases, myelogenous leukemia, myeloid leukemia, myeloproliferative disorders, nasal cavity and/or paranasal sinus cancer, nasopharyngeal carcinoma, neuroblastoma, non-Hodgkin lymphoma, non-small cell lung cancer, oral cancer, oropharyngeal cancer, osteosarcoma/malignant fibrous histiocytoma of bone, ovarian cancer, ovarian epithelial cancer, ovarian germ cell tumour, pancreatic cancer, islet cell cancer, paranasal sinus and nasal cavity cancer, parathyroid cancer, penile cancer, pharyngeal cancer, pheochromocytoma, pineal astrocytoma, pineal germinoma, pineoblastoma and/or supratentorial primitive neuroectodermal tumours, pituitary adenoma, plasma cell neoplasia/multiple myeloma, pleuropulmonary blastoma, primary central nervous system lymphoma, prostate cancer, rectal cancer, renal cell carcinoma, retinoblastoma, rhabdomyosarcoma, salivary gland cancer, Ewing sarcoma, Kaposi sarcoma, soft tissue sarcoma, uterine sarcoma, Sezary syndrome, skin cancer (non-melanoma), skin cancer (melanoma), skin carcinoma (Merkel cell), small cell lung cancer, small intestine cancer, soft tissue sarcoma, squamous cell carcinoma, squamous neck cancer with metastatic occult primary, stomach cancer, supratentorial primitive neuroectodermal tumour, T-cell lymphoma, testicular cancer, throat cancer, thymoma and/or thymic carcinoma, thyroid cancer, transitional cancer, trophoblastic tumour, ureter and/or renal pelvis cancer, urethral cancer, uterine endometrial cancer, uterine sarcoma, vaginal cancer, visual pathway and hypothalamic glioma, vulva cancer, Waldenstrom macroglobulinemia or Wilms tumour.

Kits

The present invention provides kits for preventing or treating a proliferative disease, wherein the kits comprise a therapeutically effective amount of a plant defensin, a nucleic acid, a vector, a host cell, an expression product or a pharmaceutical composition as herein disclosed.

The present invention also provides use of the kits disclosed herein for preventing or treating a proliferative disease, wherein the therapeutically effective amount of a plant defensin, a nucleic acid, a vector, a host cell, an expression product or a pharmaceutical composition as herein disclosed is administered to a subject, thereby preventing or treating the proliferative disease.

Kits of the present invention facilitate the employment of the methods of the present invention. Typically, kits for carrying out a method of the invention contain all the necessary reagents to carry out the method. For example, in one embodiment, the kit may comprise a plant defensin, a polypeptide, a polynucleotide, a vector, a host cell, an expression product or a pharmaceutical composition as herein disclosed.

Typically, the kits described herein will also comprise one or more containers. In the context of the present invention, a compartmentalised kit includes any kit in which compounds or compositions are contained in separate containers, and may include small glass containers, plastic containers or strips of plastic or paper. Such containers may allow the efficient transfer of compounds or compositions from one compartment to another compartment whilst avoiding cross-contamination of samples, and the addition of agents or solutions of each container from one compartment to another in a quantitative fashion.

Typically, a kit of the present invention will also include instructions for using the kit components to conduct the appropriate methods.

Methods and kits of the present invention are equally applicable to any animal, including humans and other animals, for example including non-human primate, equine, bovine, ovine, caprine, leporine, avian, feline and canine species. Accordingly, for application to different species, a single kit of the invention may be applicable, or alternatively different kits, for example containing compounds or compositions specific for each individual species, may be required.

Methods and kits of the present invention find application in any circumstance in which it is desirable to prevent or treat a proliferative disease.

Methods for Producing Plant Defensins with Reduced Haemolytic Activity

The present invention provides methods for producing plant defensins with reduced haemolytic activity, wherein the method comprises introducing into the plant defensin at least one alanine residue at or near the N-terminal of the defensin. The person skilled in the art would understand that several methods may be employed to achieve such addition of an N-terminal alanine, such as site-directed mutagenesis, homologous recombination, transposons and non-homologous end-joining.

Haemolytic activity may be regarded as "reduced" if the activity of the plant defensin results in relatively less hemolysis than occurs, or would reasonably be expected to occur, through use of a corresponding plant defensin that has not been modified to reduce haemolytic activity.

The present invention also provides plant defensins with reduced haemolytic activity produced by the methods disclosed herein.

Combination Therapies

Those skilled in the art will appreciate that the polypeptides, nucleic acids, vectors, host cells, expression products and compositions disclosed herein may be administered as part of a combination therapy approach, employing one or more of the polypeptides, nucleic acids, vectors, host cells, expression products and compositions disclosed herein in conjunction with other therapeutic approaches to the methods disclosed herein. For such combination therapies, each component of the combination may be administered at the same time, or sequentially in any order, or at different times, so as to provide the desired therapeutic effect. When administered separately, it may be preferred for the components to be administered by the same route of administration, although it is not necessary for this to be so. Alternatively, the components may be formulated together in a single dosage unit as a combination product. Suitable agents which may be used in combination with the compositions of the present invention will be known to those of ordinary skill in the art, and may include, for example, chemotherapeutic agents, radioisotopes and targeted therapies such as antibodies.

Chemotherapeutic agents to be used in combination with the polypeptides, nucleic acids, vectors, host cells, expression products and compositions disclosed herein may include alkylating agents such as cisplatin, carboplatin, oxaliplatin, mechlorethamine, cyclophosphamide, chlorambucil and ifosfamide, anti-metabolites such as purine or pyramidine, plant alkaloids and terpenoids such as vinca alkaloids (including vincristine, vinblastine, vinorelbine and vindesine), and taxanes (including paclitaxel and docetaxel), podophyllotoxin, topoisomerase inhibitors such as irinotecan, topotecan, amsacrine, etoposide, etoposide phosphate and teniposide, anti-neoplastics such as doxorubicin, epirubicin and bleomycin, and tyrosine kinase inhibitors.

Targeted therapies to be used in combination with the polypeptides, nucleic acids, vectors, host cells, expression products and compositions disclosed herein may include, for example, imatinib mesylate, dasatinib, nilotinib, trastuzumab, lapatinib, gefitinib, erlotinib, cetuximab, panitumumab, temsirolimus, everolimus, vorinostat, romidepsin, bexarotene, alitretinoin, tretinoin, bortezomib, pralatrexate, bevacizumab, sorafenib, sunitinib, pazopanib, rituximab, alemtuzumab, ofatumuab, tositumomab, 131I-tositumomab, ibritumomab tiuxetan, denileukin diftitox, tamoxifen, toremifene, fulvestrant, anastrozole, exemestane and letrozole.

Other therapies may also be used in combination with the polypeptides, nucleic acids, vectors, host cells, expression products and compositions disclosed herein, including, for example, surgical intervention, dietary regimes and supplements, hypnotherapy, alternative medicines and physical therapy.

Timing of Therapies

Those skilled in the art will appreciate that the polypeptides, polynucleotides, vectors, host cells, expression products and compositions disclosed herein may be administered as a single agent or as part of a combination therapy approach to the methods disclosed herein, either at diagnosis or subsequently thereafter, for example, as follow-up treatment or consolidation therapy as a compliment to currently available therapies for such treatments. The polypeptides, polynucleotides, vectors, host cells, expression products and compositions disclosed herein may also be used as preventative therapies for subjects who are genetically or environmentally predisposed to developing such diseases.

The person skilled in the art will understand and appreciate that different features disclosed herein may be combined to form combinations of features that are within the scope of the present invention.

The present invention will now be further described with reference to the following examples, which are illustrative only and non-limiting.

EXAMPLES

Materials and Methods

PCR Amplification of NoD173 from Genomic DNA

The REDExtract-N-Amp Plant PCR Kit (Sigma) was used to extract and amplify the genomic DNA encoding NoD173 from a leaf section of *Nicotiana occidentalis* ssp. *obliqua*. In brief, a crude genomic DNA preparation was prepared by incubating a piece of leaf tissue (using a standard hole-punch) in 100 μL of Extraction Solution at 95° C. for 10 min. This was followed by the addition of an equal volume of Dilution Solution. An aliquot of the diluted extract (20 μl) was then combined with the 2× REDExtract-N-Amp PCR ReadyMix (50 μl) and 4 μl each of 10 μM forward primer FLOR1 (5'-G GAA TTC TAA ACA ATG GCT CGC TCC TTG TGC-3') (SEQ ID NO: 7) and 10 μM reverse primer FLOR2 (5'-GC TCT AGA TCA GTT ATC CAT TAT CTC TTC-3') (SEQ ID NO: 8). The reaction volume was adjusted to 100 μl with the addition of sterile milliQ water. The REDExtract-N-Amp PCR ReadyMix contained the required buffer, salts, dNTPs and Taq DNA polymerase required for the PCR.

The PCR was performed with the following temperature profile: an initial cycle of 95° C., 2 min; 30 cycles of 95° C., 1 min; 55° C., 1 min; 72° C., 2 min, and a final extension cycle of 72° C. for 10 min. Following the reaction, the amplified product(s) were loaded directly onto a 1.8% (w/v) agarose gel and subjected to gel electrophoresis.

A prominent DNA band of ~800 bp was observed. It was excised from the gel, purified and cloned into the pCR2.1-TOPO vector (Invitrogen) before confirmation of its identity by DNA sequencing using primers to the flanking M13 priming sites on the plasmid. The sequencing reactions were performed at the Australian Genome and Research Facility, Melbourne. Subsequent analysis of DNA sequences was performed using the BioEdit sequence alignment editor (version 5.0.9) software (Hall TA, 1999, *Nucl Acids Symp* 41: 95-98).

Cloning of NoD173 into pPIC9 for Expression in *Pichia Pastoris*

The DNA sequence encoding the mature defensin domain of NoD173 was amplified with forward primer NoD173fw (5'-CTC GAG AM AGA GCT AGA CM TGC AAA GCA GM AG-3') (SEQ ID NO: 9) and reverse primer NoD173rv (5'-GCG GCC GCT TM CAT CGC TTA GTG CAT AGA CA-3') (SEQ ID NO: 10), using pCR2.1-TOPO-NoD173 plasmid as the DNA template, together with Phusion DNA polymerase (Finnzymes) and the corresponding buffer and dNTPs. The PCR was performed with the following temperature profile: an initial cycle of 98° C., 30 sec; 30 cycles of 98° C., 30 sec; 58° C., 30 sec; 72° C., 30 sec, and a final extension cycle of 72° C. for 10 min.

The amplified PCR product, corresponding to mature NoD173, was subsequently cloned into the pPIC9 expression vector (Invitrogen) directly in-frame with the yeast α-mating factor secretion signal using the restriction enzymes XhoI and NotI. An alanine was added to the N-terminus of the NoD173 sequence to ensure efficient cleavage of the signal at the Kex2 cleavage site. After transformation into *E. coli* TOP10 cells, the pPIC9-NoD173 plasmid was isolated and linearized using SalI to allow integration at the his4 locus of the *P. pastoris* genome. Linearized DNA was transformed into electrocompetent yeast as described by Chang et al. (2005) and His$^+$ transformants were selected for by plating onto MD agar (1.34% YNB, 4×10$^{-5}$% biotin, 1% dextrose and 1.5% agar). A single positive colony was used to inoculate 200 mL of BMG (100 mM potassium phosphate, pH 6.0, 1.34% YNB, 4×10$^{-5}$% biotin, 1% glycerol) and incubated with constant shaking at 30° C. until the $OD_{600}$ reached ~5.0. The cell mass was collected by centrifugation (1,500 g, 10 min) and resuspended into 1 L of BMM (100 mM potassium phosphate, pH 6.0, 1.34% YNB, 4×10$^{-5}$% biotin, 0.5% methanol) to a final $OD_{600}$ of 1.0 to induce expression. Expression was continued for 4 days with constant shaking at 30° C. after which time the cell mass was removed by centrifugation (10,000 g, 10 min) and the NoD173-containing supernatant was collected.

One-twentieth volume of 1 M potassium phosphate buffer (pH 6.0) was added to the supernatant and the pH was adjusted to 6.0 with the addition of 10 M KOH. The supernatant was then applied to an SP Sepharose column (GE Healthcare Biosciences) pre-equilibrated with 100 mM potassium phosphate buffer (pH 6.0). Following extensive washing with 100 mM potassium phosphate buffer (pH 6.0), the bound proteins were eluted with 100 mM potassium phosphate buffer (pH 6.0) containing 0.5 M NaCl. The eluted proteins were subsequently concentrated using Amicon Ultra 3000 MWCO centrifugal filters (Millipore) and desalted in milliQ water using the same centrifugal filters.

The protein concentration was determined using the BCA assay (Pierce) and the purity and identity of NoD173 was assessed by reducing SDS-PAGE and mass spectrometry.

Purification of NoD173 from *Nicotiana Occidentalis*

As would be known to those of skill in the art, it is also possible to isolate NoD173 from its natural source, wherein whole *N. occidentalis* flowers can be ground to a fine powder and extracted in dilute sulfuric acid as described previously (Lay et al., 2003a). Briefly, flowers can be frozen in liquid nitrogen, ground to a fine powder in a mortar and pestle, and homogenized in 50 mM sulfuric acid (3 mL per g fresh weight) for 5 min using an Ultra-Turrax homogenizer (Janke and Kunkel). After stirring for 1 h at 4° C., cellular debris can be removed by filtration through Miracloth (Calbiochem, San Diego, Calif.) and centrifugation (25,000×g, 15 min, 4° C.). The pH can then be adjusted to 7.0 by addition of 10 M NaOH and the extract can be stirred for 1 h at 4° C. before centrifugation (25,000×g, 15 min, 4° C.) to remove precipitated proteins. The supernatant (1.8 L) can be applied to an SP Sepharose™ Fast Flow (GE Healthcare Bio-Sciences) column (2.5×2.5 cm) pre-equilibrated with 10 mM sodium phosphate buffer. Unbound proteins can be removed by washing with 20 column volumes of 10 mM sodium phosphate buffer (pH 6.0) and bound proteins can be eluted in 3×10 mL fractions with 10 mM sodium phosphate buffer (pH 6.0) containing 500 mM NaCl. Samples from each purification step can be analyzed by SDS-polyacrylamide gel electrophoresis (SDS-PAGE) and immunoblotting with anti-NoD173 antibodies. Fractions from the SP Sepharose column containing NoD173 can be subjected to reverse-phase high performance liquid chromatography (RP-HPLC).

Reverse-Phase High Performance Liquid Chromatography

Figure 1:
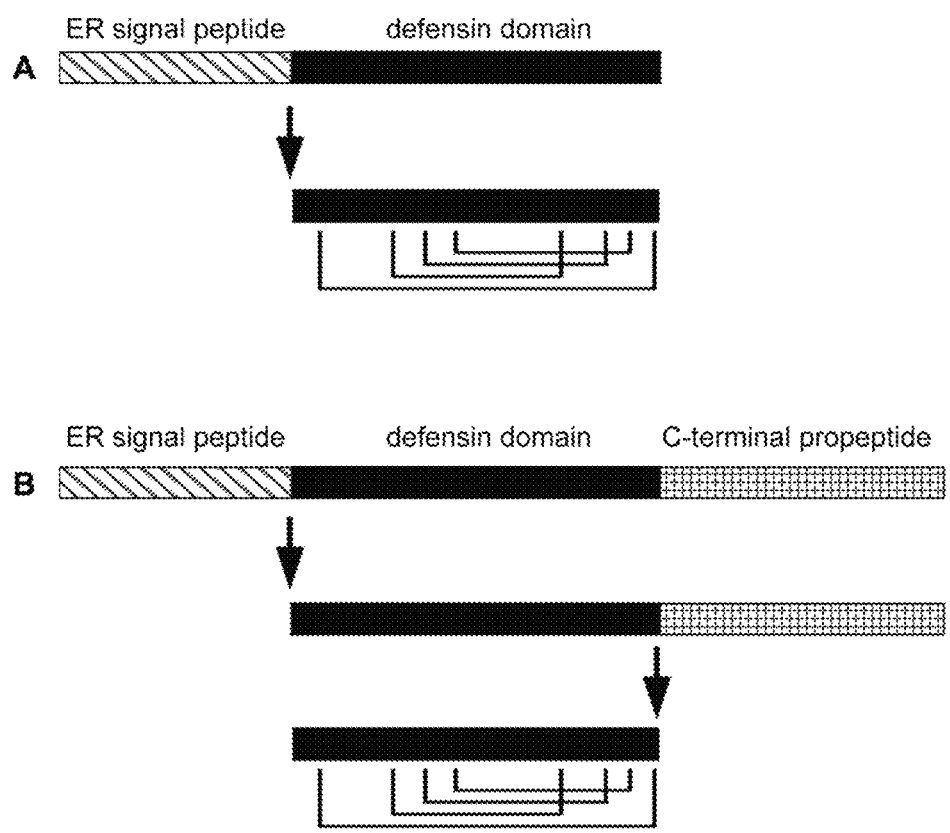
FIG. 1: is a diagrammatic representation of the structure of the precursor proteins of the two major classes of plant defensins, as predicted from cDNA clones. In the first and largest class, the precursor protein is composed of an endoplasmic reticulum (ER) signal sequence and a mature defensin domain. (1A). The second class of defensins are produced as larger precursors with C-terminal propeptides (CTPPs) (1B).
Figure 2A:
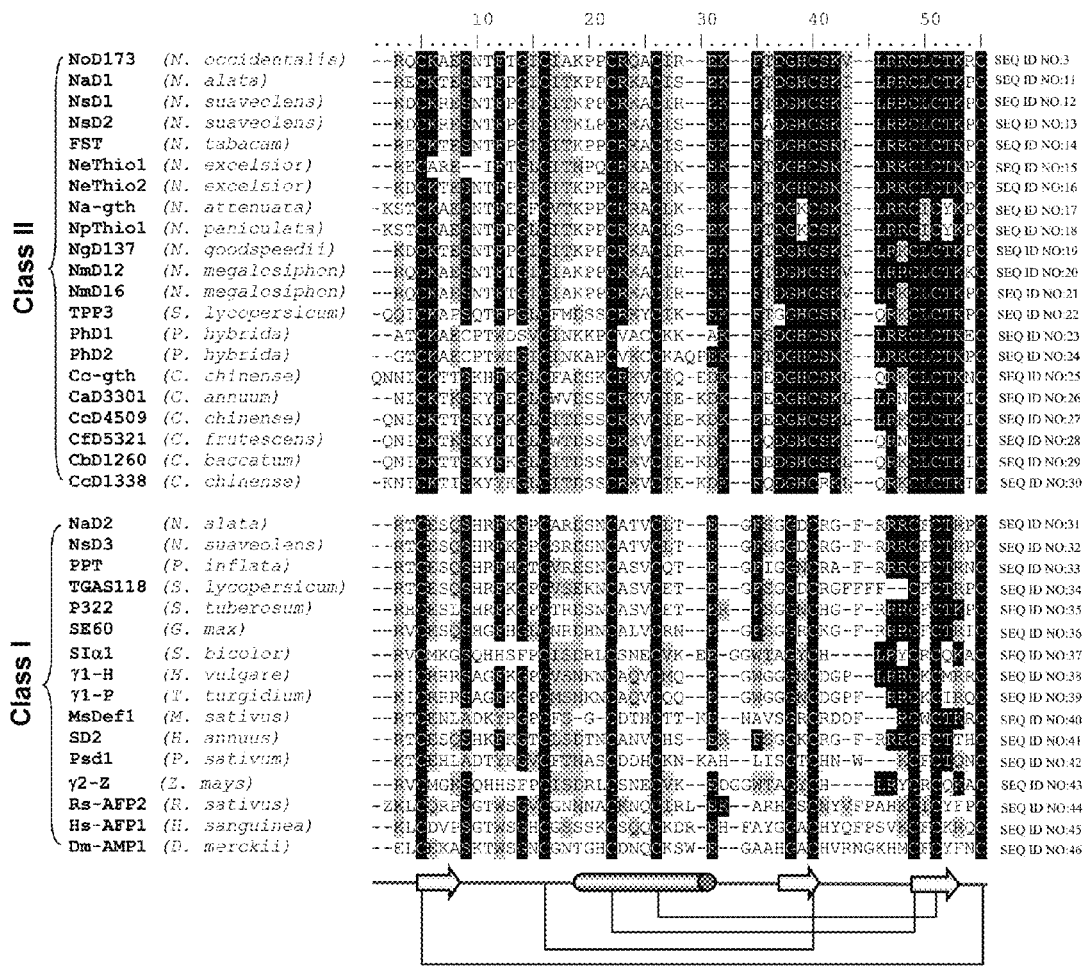

Reverse-phase high performance liquid chromatography (RP-HPLC) can be performed on a System Gold HPLC (Beckman) coupled to a detector (model 166, Beckman) using a preparative C8 column (22×250 mm, Vydac) with a guard column attached. Protein samples can be loaded in buffer A (0.1% [v/v] trifluoroacetic acid) and eluted with a linear gradient of 0-100% (v/v) buffer B (60% [v/v] acetonitrile in 0.089% [v/v] trifluoroacetic acid) at a flow rate of 10 mL/min over 40 min. Proteins can be detected by monitoring absorbance at 215 nm (FIG. 1B). Protein peaks can be collected and analyzed by SDS-PAGE.

Samples from each stage of NoD173 purification (30 μL) can be added to NuPAGE® LDS sample loading buffer (10 μL, Invitrogen) and heated to 70° C. for 10 min. The samples can then be loaded onto NuPAGE® precast 4-12% Bis-Tris polyacrylamide gels (Invitrogen) and the proteins can be separated using an XCell-Surelock electrophoresis apparatus (Invitrogen) run at 200 V. Proteins can be visualized by Coomassie Blue staining or transferred onto nitrocellulose for immunoblotting with anti-NoD173 antibodies.

Isolation of NoD173 Defensins from Seeds

As would also be known to the person skilled in the art, it is also possible to isolate NoD173 defensins from seeds, wherein *Nicotiana occidentalis* seeds (500 g) can be placed in an Ultra-Turrax homogenizer (Janke and Kunkel) and ground to a fine powder before addition of 50 mM sulfuric acid (4 mL per g fresh weight). Homogenisation can be continued for 5 min before the homogenate is transferred to a beaker and stirred for 1 h at 4° C. Cellular debris can be removed by filtration through Miracloth (Calbiochem, San Diego, Calif.) and centrifugation (25,000×g, 15 min, 4° C.). The pH can then be adjusted to 7.0 by addition of 10 M NaOH and the extract can be stirred for 1 h at 4° C. before centrifugation (25,000×g, 15 min, ° C.) to remove precipitated proteins. The supernatant can be applied to an SP-Sepharose™ Fast Flow (GE Healthcare Bio-Sciences) column (2.5×2.5 cm) pre-equilibrated with 10 mM sodium phosphate buffer. Unbound proteins can be removed by washing with 20 column volumes of 10 mM sodium phosphate buffer (pH 6.0) and bound proteins can be eluted in 3×10 mL fractions with 10 mM sodium phosphate buffer (pH 6.0) containing 500 mM NaCl.

Fractions from the SP Sepharose column can be subjected to reverse-phase high performance liquid chromatography (RP-HPLC) using, for example, an analytical Zorbax 300SB-C8 RP-HPLC column and an Agilent Technologies 1200 series system or a preparative Vydac C8 RP-HPLC column on a Beckman Coulter System Gold HPLC. Protein samples can be loaded in buffer A (0.1% (v/v) trifluoroacetic acid) and eluted with a linear gradient of 0-100% (v/v) buffer B (60% (v/v) acetonitrile in 0.089% (v/v) trifluoroacetic acid. Eluted proteins can be detected by monitoring absorbance at 215 nm. Protein peaks can be collected and defensins can be identified using SDS-PAGE and mass spectrometry.

Preparation of Reduced and Alkylated NoD173

Lyophilized NoD173 (500 μg) was dissolved in 400 μL of stock buffer (200 mM Tris-HCl pH 8.0, 2 mM EDTA, 6 M guanidine-HCl, 0.02% [v/v] Tween®-20). Reduction buffer (stock buffer with 15 mM dithiothreitol [DTT]) was added (44 μL) followed by a 4.5 h incubation at 40° C. The reaction mixture was cooled to RT before iodoacetic acid (0.5 M in 1 M NaOH, 55 μL) was added and the incubation continued in the dark for 30 min at RT. A Nanosep omega® (Registered Trademark) spin column (3K molecular weight cut off, PALL Life Sciences) was used to remove salts, DTT and iodoacetic acid and the protein concentration was determined using the BCA protein assay (Pierce). The effect of reduced and alkylated NoD173 ($NoD173_{R\&A}$) is described herein.

Cell Lines and Culture

Mammalian cell lines used in this study were as follows: mouse melanoma B16F1 cells, human umbilical vein endothelial (HUVEC) cells, the human squamous cell carcinoma cell line (A431), the human BCC cell line (CRL-7762) and human U937 myleomonocytic cells. The cells were grown in tissue culture flasks at 37° C. under a humidified atmosphere of 5% $CO_2$/95% air, and sub-cultured routinely two to three times a week according to the rate of proliferation. All mammalian cells were cultured in RPMI-1640 medium (Invitrogen) supplemented with 10% heat-inactivated fetal bovine serum (FBS, Invitrogen), 100 U/mL penicillin (Invitrogen) and 100 μg/mL streptomycin (Invitrogen), with the exception that CHO and PGS cells were cultured in DMEM-F12 medium (DMEM, Invitrogen) supplemented with 10% FBS, 100 U/mL penicillin and 100 μg/mL streptomycin. Adherent cell lines were detached from the flask by adding 3-5 mL of a mixture containing 0.25% trypsin and 0.5 μM EDTA (Invitrogen).

MTT Cell Viability Assays

Tumour cells were seeded in quadruplicate into wells of a flat-bottomed 96-well microtitre plate (50 μL) at various densities starting at $2\times10^6$ cells/mL. Four wells containing complete culture medium alone were included in each assay as a background control. The microtitre plate was incubated overnight at 37° C. under a humidified atmosphere containing 5% $CO_2$/95% air, prior to the addition of complete culture medium (100 μL) to each well and further incubated at 37° C. for 48 h. Optimum cell densities (30-50% confluency) for cell viability assays were determined for each cell line by light microscopy.

Tumour cells were seeded in a 96-well microtitre plate (50 μL/well) at an optimum density determined in the cell optimisation assay as above. Background control wells (n=8) containing the same volume of complete culture medium were included in the assay. The microtitre plate was incubated overnight at 37° C., prior to the addition of proteins at various concentrations and the plate was incubated for a further 48 h. The cell viability 3-(4,5-dimethyl-2-thiazolyl)-2,5-diphenyl-2H-tetrazolium bromide (MTT, Sigma-Aldrich) assay was carried out as follows: the MTT solution (1 mg/mL) was added to each well (100 μL) and the plate incubated for 2-3 h at 37° C. under a humidified atmosphere containing 5% $CO_2$/95% air. Subsequently, for adherent cell lines, the media was removed and replaced with dimethyl sulfoxide (100 μL, DMSO, Sigma-Aldrich), and placed on a shaker for 5 min to dissolve the tetrazolium salts. In the case of suspension cells, prior to the addition of DMSO the cells are spun at 1500 rpm for 5 min. Absorbance of each well was measured at 570 nm and the $IC_{50}$ values (the protein concentration to inhibit 50% of cell growth) were determined using the Origin Software Program.

Example 1

NoD173 Selectively Kills Tumour Cells

The effect of NoD173 on the viability of a tumour cell line and a normal human cell isolate was determined using a 3-(4,5-dimethyl-2-thiazolyl)-2,5-diphenyl-2H-tetrazolium bromide (MTT) in vitro cell culture viability assay. The cell lines tested were mouse melanoma B16F1 cells and human umbilical vein endothelial (HUVEC) cells. NoD173 was tested alongside recombinant NaD1. Cells were seeded into 96-well flat-bottomed microtitre plates at the following cell numbers: B16-F1 ($2\times10^3$/well), HUVEC ($3\times10^3$/well), and then cultured overnight. NoD173 or NaD1 were then added to cells to final concentrations ranging from 1 to 100 μM and incubated for 48 h, upon which MTT assays were carried out as described in the Materials and Methods.

NoD173 was shown to kill mouse melanoma B16F1 cells with similar efficiency to NaD1 ($IC_{50}$ 1.5 μM) as indicated by the results of the in vitro cell viability assays shown in FIG. 3. Furthermore, NoD173 was shown to be highly selective for the killing of tumour cells over normal cells. The $IC_{50}$ of NoD173 for normal human umbilical vein endothelial cells (HUVEC) was 75 µM, indicating normal cells are 50-fold more resistant to being killed than B16F1 (FIG. 4). The significant improvement of NoD173 over other class II defensins is also clearly evident when compared to NaD1 that kills HUVEC at a much lower concentration ($IC_{50}$ of 15 µM) (FIG. 4).

Example 2

NoD173 Reduces Growth of an Aggressive Solid Tumour in Vivo

The effect of NoD173 on tumour growth was assessed in an in vivo model of solid melanoma growth in mice. C57BL/6 mice were injected subcutaneously with $5 \times 10^5$ B16-F1 tumour cells and solid tumours grown to a diameter of ~10 mm. One mg/kg body weight NoD173 or $NoD173_{R\&A}$ in 50 µL of PBS, or 50 µL of PBS alone was then injected intratumuorally every 2 days until mice were sacrificed. The tumour size was measured before injection every 2 days. Six mice were used in each group.

Experimental testing of the in vivo activity of NoD173 with intratumour injection of 5 mg/kg resulted in a significant reduction in tumour growth when compared to the controls of $NoD173_{R\&A}$ and PBS alone (FIG. 5). It should be noted that the B16-F1 tumours were established at a highly advanced stage when treatment was initiated.

Example 3

Acute Subcutaneous and Intratumoural Toxicity testing of NoD173 in Mice

In vivo toxicity testing of NoD173 was undertaken using model of solid melanoma growth in mice. C57BL/6 mice were injected subcutaneously with $5 \times 10^5$ B16-F1 tumour cells and solid tumours grown to a diameter of ~10 mm. One mg/kg body weight NoD173 or $NoD173_{R\&A}$ in 50 µL of PBS, or 50 µL of PBS alone was then injected intratumourally or subcutaneously every 2 days. The tumour size was measured before injection every 2 days. Six mice were used in each group. Each of the test mice received varying amounts of NoD173/kg body weight.

The mice were observed hourly for 4 h after dosing on day 1 and at least twice daily thereafter until scheduled sacrifice. Signs of gross toxicity, adverse pharmacologic effects and behavioural changes were assessed and recorded daily as was the food and water consumption. The mice were reweighed regular intervals. On the last day of the study, the mice were sacrificed by inhalation of carbon dioxide and necropsied. All the mice received a gross pathological examination. The weights of the following organs were recorded: brain, heart, liver, lungs, kidneys, gastrointestinal tract, spleen and thymus. Subsequently, the samples were fixed in 4% (v/v) paraformaldehyde until paraffin embedding, sectioning and histopathological examination by the Australian Phenomics Network, University of Melbourne node. The gastrointestinal tract was divided into the following sections: stomach, duodenum, jejunum, ileum, cecum and colon.

All animals appeared healthy, showed no signs of gross toxicity, adverse pharmacologic effects or behavioural changes and survived to termination of the study. There was no treatment related effects on body weight, with weights closely matching that of the pre-fast weight at the commencement of the study.

No pathologies, attributable to administration of NoD173 either subcutaneously or intertumourally, were observed in any of the mice at a dose of 5 mg NoD173/kg body weight. This compares extremely favourably with previous studies showing that another plant defensin, NaD1, showed toxicity with delivery via subcutaneous, intraperitoneal or intratumoural routes at a dose above 1 mg/kg body weight.

Example 4

Basal Cell and Squamous Cell Carcinoma are Susceptible to NoD173

The effect of NoD173 on the viability of the human squamous cell carcinoma cell line (A431) and the human BCC cell line (CRL-7762) was determined using a 3-(4,5-dimethyl-2-thiazolyl)-2,5-diphenyl-2H-tetrazolium bromide (MTT) in vitro cell culture viability assay. Cells were seeded into 96-well flat-bottomed microtitre plates at the following cell numbers: B16-F1 ($2 \times 10^3$/well), HUVEC ($3 \times 10^3$/well), and then cultured overnight. NoD173 was then added to cells to final concentrations ranging from 1 to 100 µM and incubated for 48 h, upon which MTT assays were carried out as described in the Materials and Methods.

NoD173 killed CRL-7762 and A431 at low µM concentrations ($IC_{50}$ 15 µM and 10 µM, respectively) indicating that both of these non-melanoma skin cancers are sensitive to killing by NoD173 (FIGS. 6A and B).

Example 5

Functional Role of Tertiary Structure of NoD173

In order to validate the use of reduced and alkylated NoD173 as a negative control, for example as shown in FIG. 5 (labeled as "inactive"), and in order to determine the role of tertiary structure in the ability of NoD173 to permeabilize cells, U937 cells were incubated with increasing concentrations of either untreated NoD173 or reduced and alkylated NoD173 (0 to 20 µM) for 30 min at 37° C., upon which propidium iodide (PI) was then added. The number of cells that stained positively for PI (PI+) was determined by flow cytometry.

Figure 7:
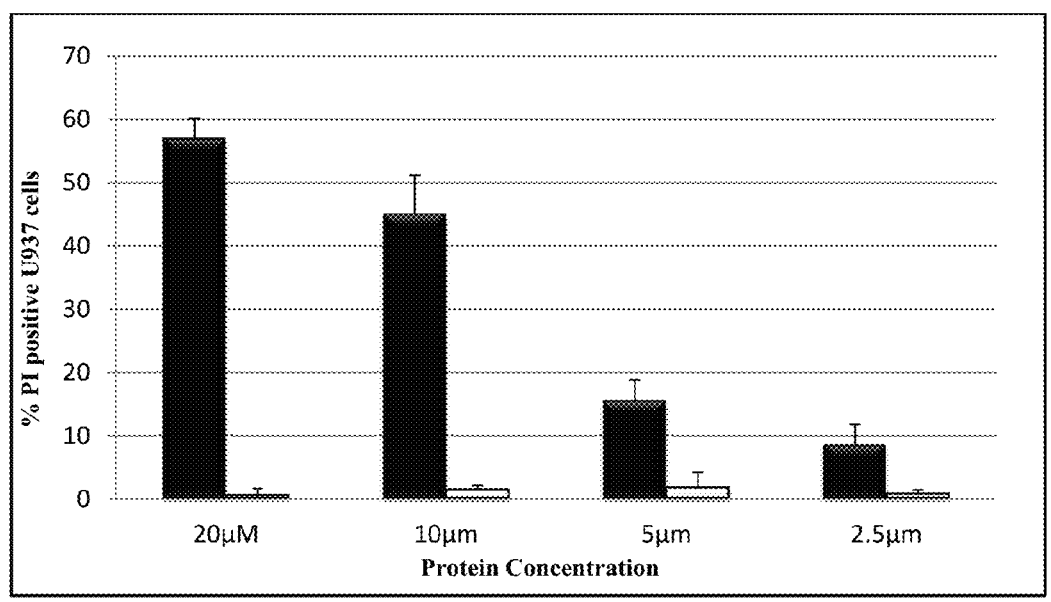
FIG. 7: shows a graphical representation of the effect of untreated NoD173 (black bars) or inactive reduced and alkylated NoD173 (white bars) on the permeabilisation of human U937 myelomonocytic cells.

As shown in FIG. 7, disruption of the tertiary structure of NoD173 by reduction and alkylation resulted in loss of function. Reduced and alkylated NoD173 was unable to permeabilise U937 cells. These data demonstrate that the tertiary structure of NoD173 is critical for its cell permeabilisation activity, and also validate the use of reduced and alkylated NoD173 as a negative control in other experiments, such as that shown in FIG. 5.

REFERENCES

Aluru et al. (1999) *Plant Physiol* 120: 633-635
Anaya-López et al. (2006) *Biotechnol Lett* 28: 1101-8
Bensch et al. (1995) *FEBS Let.* 368:331-335
Bloch et al. (1991) *FEBS Lett* 279: 101-104
Bohlmann (1994) *Crit Rev Plant Sci* 13: 1-16
Bohlmann and Apel (1991) *Annu Rev Plant Physiol Plant Mol Biol* 42: 227-240
Bonmatin et al. (1992) *J Biomol NMR* 2: 235-256
Brandstadter et al. (1996) *Mol Gen Genet* 252: 146-154
Broekaert et al. (1992) *Biochemistry* 32: 4308-4314

Broekaert et al. (1995) *Plant Physiol* 108: 1353-1358
Broekaert et al. (1997) *Crit Rev Plant Sci* 16: 297-323
Bruix et al. (1993) *Biochemistry* 32: 715-724
Cammue et al. (1992) *J Biol Chem* 267: 2228-2233
Chang et al. (2005) *Mol Biol Cell* 16: 4941-4953
Chen et al. (2002) *J Agric Food Chem* 50: 7258-63
Colilla et al. (1990) *FEBS Left* 270: 191-4
Cornet et al., (1995) *Structure* 3: 435-448
Craik et al. (1999) *J Mol Biol* 294: 1327-1336
Craik (2001) *Toxicon* 39: 1809-1813
Craik et al. (2004) *Curr Prot Pept Sci* 5: 297-315
Da Silva et al. (2003) *Protein Sci* 12: 438-446
de Zélicourt et al. (2007) *Planta* 226: 591-600
Diamond et al. (1996) *Proc Natl Acad Sci USA* 93: 5156-5160
Fehlbaum et al. (1994) *J Biol Chem* 269: 33159-33163
Ganz et al. (1985) *J Clin Invest* 76: 1427-1435
Gu et al. (1992) *Mol Gen Genet* 234: 89-96
Gustafson et al. (1994) *J Am Chem Soc* 116: 9337-9338
Hancock and Lehrer (1998) *Trends Biotech* 16: 82-88
Hanzawa et al. (1990) *FEBS Lett* 269: 413-420
Harwig et al. (1992) *Blood* 79: 1532-1537
Janssen et al. (2003) *Biochemistry* 42: 8214-8222
Jennings et al. (2001) *Proc Natl Acad Sci U.S.A.* 98: 10614-10619
Kader (1996) *Annu Rev Plant Physiol Plant Mol Biol* 47: 627-654
Kader (1997) *Trends Plant Sci* 2: 66-70
Komori et al. (1997) *Plant Physiol* 115: 314
Kushmerick et al. (1998) *FEBS Lett* 440: 302-306
Lamberty et al. (1999) *J Biol Chem* 274: 9320-9326
Lamberty et al. (2001) *Biochemistry* 40: 11995-12003
Landon et al. (1997) *Protein Sci* 6: 1878-1884
Lay and Anderson (2005) *Curr Protein Pept Sci* 6: 85-101
Lay et al. (2003a) *Plant Physiol* 131: 1283-1293
Lay et al. (2003b) *J Mol Biol* 325: 175-188
Lehrer and Ganz (2002) *Curr Opin Immunol* 14: 96-102
Lin et al. (2009) *Biosci Rep* 30: 101-109
Lobo et al. (2007) *Biochemistry* 46: 987-96
Loeza-Angeles et al. (2008) *Biotechnol Lett* 30: 1713-1719
Ma et al. (2009) *Peptides* 30: 2089-2094
Mader and Hoskin (2006) *Expert Opin Investig Drugs* 15: 933-46. Review
Marcus et al. (1997) *Eur J Biochem* 244: 743-749
McManus et al. (1999) *J Mol Biol* 293: 629-638
Melo et al. (2002) *Proteins* 48: 311-319
Mendez et al. (1990) *Eur J Biochem* 194: 533-539
Mendez et al. (1996) *Eur J Biochem* 239: 67-73
Milligan et al. (1995) *Plant Mol Biol* 28: 691-711
Mirouze et al. (2006) *Plant J* 47: 329-342
Moreno et al. (1994) *Eur J Biochem* 223: 135-139
Ngai and Ng (2005) *Biochem Cell Biol* 83: 212-20
Osborn et al. (1995) *FEBS Lett* 368: 257-262
Patel et al. (1998) *Biochemistry* 37: 983-990
Pelegrini and Franco (2005) *Int J Biochem Cell Biol* 37: 2239-53
Ramamoorthy et al. (2007) *Mol Microbiol* 66: 771-786
Russell et al. (1996) *Infect Immun* 64: 1565-1568
Segura et al. (1998) *FEBS Lett* 435:159-162
Selsted et al. (1985) *J Clin Invest* 76: 1436-1439
Selsted et al. (1993) *J Biol Chem* 268: 6641-6648
Tailor et al. (1997) *J Biol Chem* 272: 24480-24487
Tam et al. (1999) *Proc Natl Acad Sci U.S.A.* 96: 8913-8918
Tang and Selsted (1993) *J Biol Chem* 268: 6649-6653
Tang et al. (1999a) *Science* 286: 498-502
Tang et al. (1999b) *Infect Immun* 67: 6139-6144
Tarver et al. (1998) *Infect Immun* 66: 1045-1056
Terras et al. (1992) *J Biol Chem* 267: 15301-15309
Terras et al. (1993) *FEBS Lett* 316: 233-240
Terras et al. (1995) *Plant Cell* 7: 573-588
Thomma et al. (2003) *Curr Drug Targets—Infect. Dis.* 3: 1-8
Trabi et al. (2001) *Biochemistry* 40: 4211-4221
van der Weerden (2008) *J Biol Chem* 283: 14445-14452
Wijaya et al. (2000) *Plant Sci* 159: 243-255
Wong and Ng (2005) *Int J Biochem Cell Biol* 37: 1626-32
Yamada et al. (1997) *Plant Physiol* 115: 314
Zhang and Lewis (1997) *FEMS Microbiol Lett* 149: 59-64
Zhang et al. (1997) *Cereal Chem* 74: 119-122

---

The invention claimed is:

1. A method for treating skin cancer in a subject in need thereof comprising administering to the subject a therapeutically effective amount of a polypeptide having eight canonical cysteine residues in the configuration of $CyS_I$-$CyS_{VIII}$, $CyS_{II}$-$CyS_V$, $CyS_{III}$-$CyS_{VI}$ and $CyS_{IV}$-$CyS_{VII}$ that (a) comprises a first amino acid sequence set forth as SEQ ID NOs: 1, 3 or 5, or (b) comprises a second amino acid sequence sharing not less than 95% identity to the first amino acid sequence, or a host cell comprising the polypeptide; or an isolated expression product comprising the polypeptide;

or a pharmaceutical composition comprising the polypeptide, the host cell, or the isolated expression product, together with a pharmaceutically acceptable carrier, diluent or excipient.

2. The method according to claim 1, wherein the cancer is selected from the group consisting of basal cell carcinoma, squamous cell carcinoma, and melanoma.

* * * * *

UNITED STATES PATENT AND TRADEMARK OFFICE
CERTIFICATE OF CORRECTION

PATENT NO. : 9,540,423 B2  
APPLICATION NO. : 14/352360  
DATED : January 10, 2017  
INVENTOR(S) : Mark Darren Hulett and Fung Tso Lay Page 1 of 1

It is certified that error appears in the above-identified patent and that said Letters Patent is hereby corrected as shown below:

In the Specification  
Column 2, Line 58 - "$Cys_{II}$-$Cys_{IV}$" should be --$Cys_{II}$-$Cys_{V}$--.  
Column 2, Line 59 - "$Cys_{V}$-$Cys_{VII}$" should be --$Cys_{IV}$-$Cys_{VII}$--.  
Column 5, Line 26 - "Comet" should be --Cornet--.  
Column 7, Line 43 - "lathe" should be --to the--.  
Column 14, Line 33 - "$Cys_{IV}$, $Cys_{III}$-$Cys_{VI}$ and $Cys_{V}$-$Cys_{VII}$" should be --$Cys_{V}$, $Cys_{III}$-$Cys_{VI}$ and $Cys_{IV}$-$Cys_{VII}$--.  
Column 23, Line 44 - "AM" should read --AAA--.  
Column 23, Line 44 - "CM" should read --CAA--.  
Column 23, Line 45 - "GM" should read --CAA--.  
Column 23, Line 46 - "TM" should read --TAA--.

Signed and Sealed this  
Twenty-second Day of August, 2017

Joseph Matal  
*Performing the Functions and Duties of the*  
*Under Secretary of Commerce for Intellectual Property and*  
*Director of the United States Patent and Trademark Office*

SEQUENCE LISTING

```
<160> NUMBER OF SEQ ID NOS: 46

<210> SEQ ID NO 1
<211> LENGTH: 105
<212> TYPE: PRT
<213> ORGANISM: Nicotiana occidentalis

<400> SEQUENCE: 1

Met Ala Arg Ser Leu Cys Phe Met Gly Phe Ala Ile Leu Ala Met Met
1               5                   10                  15

Leu Phe Val Ala Tyr Glu Val Gln Ala Arg Gln Cys Lys Ala Glu Ser
                20                  25                  30

Asn Thr Phe Thr Gly Ile Cys Ile Ala Lys Pro Pro Cys Arg Gln Ala
            35                  40                  45

Cys Ile Arg Glu Lys Phe Thr Asp Gly His Cys Ser Lys Val Leu Arg
    50                  55                  60

Arg Cys Leu Cys Thr Lys Arg Cys Val Phe Asp Glu Lys Met Ile Glu
65                  70                  75                  80

Thr Gly Ala Glu Thr Leu Ala Glu Glu Ala Lys Thr Phe Ala Ala Ala
                85                  90                  95

Leu Leu Glu Glu Glu Ile Met Asp Asn
```

<210> SEQ ID NO 2
<211> LENGTH: 318
<212> TYPE: DNA
<213> ORGANISM: Nicotiana occidentalis

<400> SEQUENCE: 2

```
atggctcgct ccttgtgctt catgggattt gctatcttgg caatgatgct ctttgttgcc    60
tatgaggtgc aagctagaca tgcaaagca gaaagcaata cattcactgg aatatgcatt   120
gccaaaccac catgcagaca agcttgtatc cgtgagaaat ttactgatgg tcattgtagc   180
aaagtcctca gaaggtgtct atgcactaag cgatgtgtgt tgatgagaa gatgatcgaa   240
acaggagctg aaaccttagc tgaggaagca aaaactttg ctgcagcttt gcttgaagaa   300
gagataatgg ataactga                                                318
```

<210> SEQ ID NO 3
<211> LENGTH: 47
<212> TYPE: PRT
<213> ORGANISM: Nicotiana occidentalis

<400> SEQUENCE: 3

```
Arg Gln Cys Lys Ala Glu Ser Asn Thr Phe Thr Gly Ile Cys Ile Ala
1               5                   10                  15
Lys Pro Pro Cys Arg Gln Ala Cys Ile Arg Glu Lys Phe Thr Asp Gly
            20                  25                  30
His Cys Ser Lys Val Leu Arg Arg Cys Leu Cys Thr Lys Arg Cys
        35                  40                  45
```

<210> SEQ ID NO 4
<211> LENGTH: 141
<212> TYPE: DNA
<213> ORGANISM: Nicotiana occidentalis

<400> SEQUENCE: 4

```
agacaatgca agcagaaag caatacattc actggaatat gcattgccaa accaccatgc    60
agacaagctt gtatccgtga aaatttact gatggtcatt gtagcaaagt cctcagaagg   120
tgtctatgca ctaagcgatg t                                            141
```

<210> SEQ ID NO 5
<211> LENGTH: 48
<212> TYPE: PRT
<213> ORGANISM: Artificial Sequence
<220> FEATURE:
<223> OTHER INFORMATION: Synthetic

<400> SEQUENCE: 5

```
Ala Arg Gln Cys Lys Ala Glu Ser Asn Thr Phe Thr Gly Ile Cys Ile
1               5                   10                  15
Ala Lys Pro Pro Cys Arg Gln Ala Cys Ile Arg Glu Lys Phe Thr Asp
            20                  25                  30
Gly His Cys Ser Lys Val Leu Arg Arg Cys Leu Cys Thr Lys Arg Cys
        35                  40                  45
```

<210> SEQ ID NO 6
<211> LENGTH: 144
<212> TYPE: DNA
<213> ORGANISM: Artificial Sequence
<220> FEATURE:
<223> OTHER INFORMATION: Synthetic

```
<400> SEQUENCE: 6
gctagacaat gcaaagcaga aagcaataca ttcactggaa tatgcattgc caaaccacca      60
tgcagacaag cttgtatccg tgagaaattt actgatggtc attgtagcaa agtcctcaga    120
aggtgtctat gcactaagcg atgt                                           144

<210> SEQ ID NO 7
<211> LENGTH: 31
<212> TYPE: DNA
<213> ORGANISM: Nicotiana occidentalis

<400> SEQUENCE: 7
ggaattctaa acaatggctc gctccttgtg c                                    31

<210> SEQ ID NO 8
<211> LENGTH: 29
<212> TYPE: DNA
<213> ORGANISM: Nicotiana occidentalis

<400> SEQUENCE: 8
gctctagatc agttatccat tatctcttc                                       29

<210> SEQ ID NO 9
<211> LENGTH: 35
<212> TYPE: DNA
<213> ORGANISM: Nicotiana occidentalis

<400> SEQUENCE: 9
ctcgagaaaa gagctagaca atgcaaagca gaaag                                35

<210> SEQ ID NO 10
<211> LENGTH: 32
<212> TYPE: DNA
<213> ORGANISM: Nicotiana occidentalis

<400> SEQUENCE: 10
gcggccgctt aacatcgctt agtgcataga ca                                   32

<210> SEQ ID NO 11
<211> LENGTH: 47
<212> TYPE: PRT
<213> ORGANISM: Nicotiana alata

<400> SEQUENCE: 11

Arg Glu Cys Lys Thr Glu Ser Asn Thr Phe Pro Gly Ile Cys Ile Thr
1               5                   10                  15

Lys Pro Pro Cys Arg Lys Ala Cys Ile Ser Glu Lys Phe Thr Asp Gly
            20                  25                  30

His Cys Ser Lys Ile Leu Arg Arg Cys Leu Cys Thr Lys Pro Cys
        35                  40                  45

<210> SEQ ID NO 12
<211> LENGTH: 47
<212> TYPE: PRT
<213> ORGANISM: Nicotiana suaveolens

<400> SEQUENCE: 12

Lys Asp Cys Lys Arg Glu Ser Asn Thr Phe Pro Gly Ile Cys Ile Thr
1               5                   10                  15

Lys Pro Pro Cys Arg Lys Ala Cys Ile Arg Glu Lys Phe Thr Asp Gly
            20                  25                  30
```

```
His Cys Ser Lys Ile Leu Arg Arg Cys Leu Cys Thr Lys Pro Cys
        35                  40                  45
```

<210> SEQ ID NO 13
<211> LENGTH: 47
<212> TYPE: PRT
<213> ORGANISM: Nicotiana suaveolens

<400> SEQUENCE: 13

```
Lys Asp Cys Lys Arg Glu Ser Asn Thr Phe Pro Gly Ile Cys Ile Thr
1               5                   10                  15

Lys Leu Pro Cys Arg Lys Ala Cys Ile Ser Glu Lys Phe Ala Asp Gly
            20                  25                  30

His Cys Ser Lys Ile Leu Arg Arg Cys Leu Cys Thr Lys Pro Cys
        35                  40                  45
```

<210> SEQ ID NO 14
<211> LENGTH: 47
<212> TYPE: PRT
<213> ORGANISM: Nicotiana tabacum

<400> SEQUENCE: 14

```
Arg Glu Cys Lys Thr Glu Ser Asn Thr Phe Pro Gly Ile Cys Ile Thr
1               5                   10                  15

Lys Pro Pro Cys Arg Lys Ala Cys Ile Ser Glu Lys Phe Thr Asp Gly
            20                  25                  30

His Cys Ser Lys Ile Leu Arg Arg Cys Leu Cys Thr Lys Pro Cys
        35                  40                  45
```

<210> SEQ ID NO 15
<211> LENGTH: 45
<212> TYPE: PRT
<213> ORGANISM: Nicotiana excelsior

<400> SEQUENCE: 15

```
Arg Glu Cys Ala Arg Glu Ile Phe Thr Gly Leu Cys Ile Thr Asn Pro
1               5                   10                  15

Gln Cys Arg Lys Ala Cys Ile Lys Glu Lys Phe Thr Asp Gly His Cys
            20                  25                  30

Ser Lys Ile Leu Arg Arg Cys Leu Cys Thr Lys Pro Cys
        35                  40                  45
```

<210> SEQ ID NO 16
<211> LENGTH: 47
<212> TYPE: PRT
<213> ORGANISM: Nicotiana excelsior

<400> SEQUENCE: 16

```
Lys Asp Cys Lys Thr Glu Ser Asn Thr Phe Pro Gly Ile Cys Ile Thr
1               5                   10                  15

Lys Pro Pro Cys Arg Lys Ala Cys Ile Lys Glu Lys Phe Thr Asp Gly
            20                  25                  30

His Cys Ser Lys Ile Leu Arg Arg Cys Leu Cys Thr Lys Pro Cys
        35                  40                  45
```

<210> SEQ ID NO 17
<211> LENGTH: 48
<212> TYPE: PRT
<213> ORGANISM: Nicotiana attenuata

<400> SEQUENCE: 17

```
Lys Ser Thr Cys Lys Ala Glu Ser Asn Thr Phe Glu Gly Phe Cys Val
1               5                   10                  15

Thr Lys Pro Pro Cys Arg Lys Ala Cys Leu Lys Glu Lys Phe Thr Asp
            20                  25                  30

Gly Lys Cys Ser Lys Ile Leu Arg Arg Cys Ile Cys Tyr Lys Pro Cys
            35                  40                  45
```

<210> SEQ ID NO 18
<211> LENGTH: 48
<212> TYPE: PRT
<213> ORGANISM: Nicotiana paniculata

<400> SEQUENCE: 18

```
Lys Ser Thr Cys Lys Ala Glu Ser Asn Thr Phe Pro Gly Leu Cys Ile
1               5                   10                  15

Thr Lys Pro Pro Cys Arg Lys Ala Cys Leu Ser Glu Lys Phe Thr Asp
            20                  25                  30

Gly Lys Cys Ser Lys Ile Leu Arg Arg Cys Ile Cys Tyr Lys Pro Cys
            35                  40                  45
```

<210> SEQ ID NO 19
<211> LENGTH: 47
<212> TYPE: PRT
<213> ORGANISM: Nicotiana goodspeedii

<400> SEQUENCE: 19

```
Lys Asp Cys Lys Thr Glu Ser Asn Thr Phe Pro Gly Ile Cys Ile Thr
1               5                   10                  15

Lys Pro Pro Cys Arg Lys Ala Cys Ile Arg Glu Lys Phe Thr Asp Gly
            20                  25                  30

His Cys Ser Lys Ile Leu Arg Lys Cys Leu Cys Thr Lys Pro Cys
            35                  40                  45
```

<210> SEQ ID NO 20
<211> LENGTH: 47
<212> TYPE: PRT
<213> ORGANISM: Nicotiana megalosiphon

<400> SEQUENCE: 20

```
Arg Gln Cys Lys Ala Glu Ser Asn Thr Phe Thr Gly Ile Cys Ile Ala
1               5                   10                  15

Lys Pro Pro Cys Arg Lys Ala Cys Ile Arg Glu Lys Phe Thr Asp Gly
            20                  25                  30

His Cys Ser Lys Val Leu Arg Arg Cys Leu Cys Thr Lys Lys Cys
            35                  40                  45
```

<210> SEQ ID NO 21
<211> LENGTH: 47
<212> TYPE: PRT
<213> ORGANISM: Nicotiana megalosiphon

<400> SEQUENCE: 21

```
Arg Gln Cys Lys Ala Glu Ser Asn Thr Phe Thr Gly Ile Cys Ile Ala
1               5                   10                  15

Lys Pro Pro Cys Arg Lys Ala Cys Ile Arg Glu Lys Phe Thr Asp Gly
            20                  25                  30

His Cys Ser Lys Val Leu Arg Lys Cys Leu Cys Thr Lys Pro Cys
            35                  40                  45
```

<210> SEQ ID NO 22
<211> LENGTH: 48
<212> TYPE: PRT
<213> ORGANISM: Solanum lycopersicum

<400> SEQUENCE: 22

Gln Gln Ile Cys Lys Ala Pro Ser Gln Thr Phe Pro Gly Leu Cys Phe
1               5                   10                  15

Met Asp Ser Ser Cys Arg Lys Tyr Cys Ile Lys Glu Lys Phe Thr Gly
            20                  25                  30

Gly His Cys Ser Lys Leu Gln Arg Lys Cys Leu Cys Thr Lys Pro Cys
        35                  40                  45

<210> SEQ ID NO 23
<211> LENGTH: 47
<212> TYPE: PRT
<213> ORGANISM: Petunia x hybrida

<400> SEQUENCE: 23

Ala Thr Cys Lys Ala Glu Cys Pro Thr Trp Asp Ser Val Cys Ile Asn
1               5                   10                  15

Lys Lys Pro Cys Val Ala Cys Cys Lys Lys Ala Lys Phe Ser Asp Gly
            20                  25                  30

His Cys Ser Lys Ile Leu Arg Arg Cys Leu Cys Thr Lys Glu Cys
        35                  40                  45

<210> SEQ ID NO 24
<211> LENGTH: 49
<212> TYPE: PRT
<213> ORGANISM: Petunia x hybrida

<400> SEQUENCE: 24

Gly Thr Cys Lys Ala Glu Cys Pro Thr Trp Glu Gly Ile Cys Ile Asn
1               5                   10                  15

Lys Ala Pro Cys Val Lys Cys Cys Lys Ala Gln Pro Glu Lys Phe Thr
            20                  25                  30

Asp Gly His Cys Ser Lys Ile Leu Arg Arg Cys Leu Cys Thr Lys Pro
        35                  40                  45

Cys

<210> SEQ ID NO 25
<211> LENGTH: 50
<212> TYPE: PRT
<213> ORGANISM: Capsicum chinense

<400> SEQUENCE: 25

Gln Asn Asn Ile Cys Lys Thr Thr Ser Lys His Phe Lys Gly Leu Cys
1               5                   10                  15

Phe Ala Asp Ser Lys Cys Arg Lys Val Cys Ile Gln Glu Asp Lys Phe
            20                  25                  30

Glu Asp Gly His Cys Ser Lys Leu Gln Arg Lys Cys Leu Cys Thr Lys
        35                  40                  45

Asn Cys
    50

<210> SEQ ID NO 26
<211> LENGTH: 48
<212> TYPE: PRT
<213> ORGANISM: Capsicum annuum

<400> SEQUENCE: 26

-continued

Asn Ile Cys Lys Thr Lys Ser Lys Tyr Phe Glu Gly Leu Cys Trp Val
1               5                   10                  15

Asp Ser Ser Cys Arg Lys Val Cys Ile Glu Lys Asp Lys Phe Glu Asp
                20                  25                  30

Gly His Cys Ser Lys Leu Leu Arg Asn Cys Leu Cys Thr Lys Ile Cys
            35                  40                  45

<210> SEQ ID NO 27
<211> LENGTH: 49
<212> TYPE: PRT
<213> ORGANISM: Capsicum chinense

<400> SEQUENCE: 27

Gln Asn Ile Cys Lys Thr Thr Ser Lys Tyr Phe Lys Gly Leu Cys Ile
1               5                   10                  15

Thr Asp Ser Ser Cys Arg Lys Val Cys Ile Glu Lys Asp Lys Phe Glu
                20                  25                  30

Asp Gly His Cys Ser Lys Leu Leu Arg Lys Cys Leu Cys Thr Lys Ile
            35                  40                  45

Cys

<210> SEQ ID NO 28
<211> LENGTH: 49
<212> TYPE: PRT
<213> ORGANISM: Capsicum frutescens

<400> SEQUENCE: 28

Gln Asn Ile Cys Lys Thr Lys Ser Lys Tyr Phe Thr Gly Leu Cys Trp
1               5                   10                  15

Thr Asp Ser Ser Cys Arg Lys Val Cys Ile Glu Lys Asp Lys Phe Gln
                20                  25                  30

Asp Gly His Cys Ser Lys Ile Gln Arg Asn Cys Leu Cys Thr Lys Ile
            35                  40                  45

Cys

<210> SEQ ID NO 29
<211> LENGTH: 49
<212> TYPE: PRT
<213> ORGANISM: Capsicum baccatum

<400> SEQUENCE: 29

Gln Asn Ile Cys Lys Thr Thr Ser Lys Tyr Phe Lys Gly Leu Cys Ile
1               5                   10                  15

Thr Asp Ser Ser Cys Arg Lys Val Cys Ile Glu Lys Asp Lys Phe Glu
                20                  25                  30

Asp Gly His Cys Ser Lys Leu Gln Arg Lys Cys Leu Cys Thr Lys Ile
            35                  40                  45

Cys

<210> SEQ ID NO 30
<211> LENGTH: 49
<212> TYPE: PRT
<213> ORGANISM: Capsicum chinense

<400> SEQUENCE: 30

Lys Asn Ile Cys Lys Thr Ile Ser Lys Tyr Tyr Lys Gly Leu Cys Ile
1               5                   10                  15

Thr Asp Ser Ser Cys Arg Lys Val Cys Ile Glu Lys Asp Lys Phe Gln

```
                    20                  25                  30

Asp Gly His Cys Arg Lys Leu Gln Arg Lys Cys Leu Cys Thr Lys Ile
            35                  40                  45

Cys

<210> SEQ ID NO 31
<211> LENGTH: 47
<212> TYPE: PRT
<213> ORGANISM: Nicotiana alata

<400> SEQUENCE: 31

Arg Thr Cys Glu Ser Gln Ser His Arg Phe Lys Gly Pro Cys Ala Arg
1               5                   10                  15

Asp Ser Asn Cys Ala Thr Val Cys Leu Thr Glu Gly Phe Ser Gly Gly
            20                  25                  30

Asp Cys Arg Gly Phe Arg Arg Arg Cys Phe Cys Thr Arg Pro Cys
            35                  40                  45

<210> SEQ ID NO 32
<211> LENGTH: 47
<212> TYPE: PRT
<213> ORGANISM: Nicotiana suaveolens

<400> SEQUENCE: 32

Arg Thr Cys Glu Ser Gln Ser His Arg Phe Lys Gly Pro Cys Ser Arg
1               5                   10                  15

Asp Ser Asn Cys Ala Thr Val Cys Leu Thr Glu Gly Phe Ser Gly Gly
            20                  25                  30

Asp Cys Arg Gly Phe Arg Arg Arg Cys Phe Cys Thr Arg Pro Cys
            35                  40                  45

<210> SEQ ID NO 33
<211> LENGTH: 47
<212> TYPE: PRT
<213> ORGANISM: Phytophthora inflata

<400> SEQUENCE: 33

Arg Thr Cys Glu Ser Gln Ser His Arg Phe His Gly Thr Cys Val Arg
1               5                   10                  15

Glu Ser Asn Cys Ala Ser Val Cys Gln Thr Glu Gly Phe Ile Gly Gly
            20                  25                  30

Asn Cys Arg Ala Phe Arg Arg Arg Cys Phe Cys Thr Arg Asn Cys
            35                  40                  45

<210> SEQ ID NO 34
<211> LENGTH: 47
<212> TYPE: PRT
<213> ORGANISM: Solanum lycopersicum

<400> SEQUENCE: 34

Arg Thr Cys Glu Ser Gln Ser His Arg Phe Lys Gly Pro Cys Val Ser
1               5                   10                  15

Glu Lys Asn Cys Ala Ser Val Cys Glu Thr Glu Gly Phe Ser Gly Gly
            20                  25                  30

Asp Cys Arg Gly Phe Phe Phe Arg Cys Phe Cys Thr Arg Pro Cys
            35                  40                  45

<210> SEQ ID NO 35
<211> LENGTH: 47
<212> TYPE: PRT
```

<213> ORGANISM: Symphytum tuberosum

<400> SEQUENCE: 35

Arg His Cys Glu Ser Leu Ser His Arg Phe Lys Gly Pro Cys Thr Arg
1               5                   10                  15

Asp Ser Asn Cys Ala Ser Val Cys Glu Thr Glu Arg Phe Ser Gly Gly
            20                  25                  30

Asn Cys His Gly Phe Arg Arg Arg Cys Phe Cys Thr Lys Pro Cys
        35                  40                  45

<210> SEQ ID NO 36
<211> LENGTH: 47
<212> TYPE: PRT
<213> ORGANISM: Glycine max

<400> SEQUENCE: 36

Arg Val Cys Glu Ser Gln Ser His Gly Phe His Gly Leu Cys Asn Arg
1               5                   10                  15

Asp His Asn Cys Ala Leu Val Cys Arg Asn Glu Gly Phe Ser Gly Gly
            20                  25                  30

Arg Cys Lys Gly Phe Arg Arg Arg Cys Phe Cys Thr Arg Ile Cys
        35                  40                  45

<210> SEQ ID NO 37
<211> LENGTH: 47
<212> TYPE: PRT
<213> ORGANISM: Sorghum bicolor

<400> SEQUENCE: 37

Arg Val Cys Met Lys Gly Ser Gln His His Ser Phe Pro Cys Ile Ser
1               5                   10                  15

Asp Arg Leu Cys Ser Asn Glu Cys Val Lys Glu Glu Gly Gly Trp Thr
            20                  25                  30

Ala Gly Tyr Cys His Leu Arg Tyr Cys Arg Cys Gln Lys Ala Cys
        35                  40                  45

<210> SEQ ID NO 38
<211> LENGTH: 47
<212> TYPE: PRT
<213> ORGANISM: Hordeum vulgare

<400> SEQUENCE: 38

Arg Ile Cys Arg Arg Arg Ser Ala Gly Phe Lys Gly Pro Cys Val Ser
1               5                   10                  15

Asn Lys Asn Cys Ala Gln Val Cys Met Gln Glu Gly Trp Gly Gly Gly
            20                  25                  30

Asn Cys Asp Gly Pro Leu Arg Arg Cys Lys Cys Met Arg Arg Cys
        35                  40                  45

<210> SEQ ID NO 39
<211> LENGTH: 47
<212> TYPE: PRT
<213> ORGANISM: Triticum turgidum

<400> SEQUENCE: 39

Lys Ile Cys Arg Arg Arg Ser Ala Gly Phe Lys Gly Pro Cys Met Ser
1               5                   10                  15

Asn Lys Asn Cys Ala Gln Val Cys Gln Gln Glu Gly Trp Gly Gly Gly
            20                  25                  30

Asn Cys Asp Gly Pro Phe Arg Arg Cys Lys Cys Ile Arg Gln Cys 35                  40                  45

<210> SEQ ID NO 40
<211> LENGTH: 45
<212> TYPE: PRT
<213> ORGANISM: Medicago sativa

<400> SEQUENCE: 40

Arg Thr Cys Glu Asn Leu Ala Asp Lys Tyr Arg Gly Pro Cys Phe Ser
1               5                   10                  15

Gly Cys Asp Thr His Cys Thr Thr Lys Glu Asn Ala Val Ser Gly Arg
            20                  25                  30

Cys Arg Asp Asp Phe Arg Cys Trp Cys Thr Lys Arg Cys
        35                  40                  45

<210> SEQ ID NO 41
<211> LENGTH: 47
<212> TYPE: PRT
<213> ORGANISM: Helianthus annuus

<400> SEQUENCE: 41

Arg Thr Cys Glu Ser Gln Ser His Lys Phe Lys Gly Thr Cys Leu Ser
1               5                   10                  15

Asp Thr Asn Cys Ala Asn Val Cys His Ser Glu Arg Phe Ser Gly Gly
            20                  25                  30

Lys Cys Arg Gly Phe Arg Arg Arg Cys Phe Cys Thr Thr His Cys
        35                  40                  45

<210> SEQ ID NO 42
<211> LENGTH: 46
<212> TYPE: PRT
<213> ORGANISM: Pisum sativum

<400> SEQUENCE: 42

Lys Thr Cys Glu His Leu Ala Asp Thr Tyr Arg Gly Val Cys Phe Thr
1               5                   10                  15

Asn Ala Ser Cys Asp Asp His Cys Lys Asn Lys Ala His Leu Ile Ser
            20                  25                  30

Gly Thr Cys His Asn Trp Lys Cys Phe Cys Thr Gln Asn Cys
        35                  40                  45

<210> SEQ ID NO 43
<211> LENGTH: 47
<212> TYPE: PRT
<213> ORGANISM: Zea mays

<400> SEQUENCE: 43

Arg Val Cys Met Gly Lys Ser Gln His His Ser Phe Pro Cys Ile Ser
1               5                   10                  15

Asp Arg Leu Cys Ser Asn Glu Cys Val Lys Glu Asp Gly Gly Trp Thr
            20                  25                  30

Ala Gly Tyr Cys His Leu Arg Tyr Cys Arg Cys Gln Lys Ala Cys
        35                  40                  45

<210> SEQ ID NO 44
<211> LENGTH: 51
<212> TYPE: PRT
<213> ORGANISM: Raphanus sativus

<400> SEQUENCE: 44

Glx Lys Leu Cys Gln Arg Pro Ser Gly Thr Trp Ser Gly Val Cys Gly

-continued

```
                1               5                    10                   15
Asn Asn Asn Ala Cys Arg Asn Gln Cys Ile Arg Leu Glu Lys Ala Arg
                    20                  25                  30

His Gly Ser Cys Asn Tyr Val Phe Pro Ala His Lys Cys Ile Cys Tyr
            35                  40                  45

Phe Pro Cys
        50

<210> SEQ ID NO 45
<211> LENGTH: 51
<212> TYPE: PRT
<213> ORGANISM: Heuchera sanguinea

<400> SEQUENCE: 45

Lys Leu Cys Asp Val Pro Ser Gly Thr Trp Ser Gly His Cys Gly Ser
1               5                   10                  15

Ser Ser Lys Cys Ser Gln Gln Cys Lys Asp Arg Glu His Phe Ala Tyr
                20                  25                  30

Gly Gly Ala Cys His Tyr Gln Phe Pro Ser Val Lys Cys Phe Cys Lys
            35                  40                  45

Arg Gln Cys
        50

<210> SEQ ID NO 46
<211> LENGTH: 50
<212> TYPE: PRT
<213> ORGANISM: Dahlia merckii

<400> SEQUENCE: 46

Glu Leu Cys Glu Lys Ala Ser Lys Thr Trp Ser Gly Asn Cys Gly Asn
1               5                   10                  15

Thr Gly His Cys Asp Asn Gln Cys Lys Ser Trp Glu Gly Ala Ala His
                20                  25                  30

Gly Ala Cys His Val Arg Asn Gly Lys His Met Cys Phe Cys Tyr Phe
            35                  40                  45

Asn Cys
    50
```